(12) United States Patent
Klingler et al.

(10) Patent No.: US 6,472,562 B1
(45) Date of Patent: Oct. 29, 2002

(54) N-GUANIDINOALKYLAMIDES, THEIR PREPARATION, THEIR USE, AND PHARMACEUTICAL PREPARATIONS COMPRISING THEM

(75) Inventors: Otmar Klingler, Rodgau (DE); Gerhard Zoller, Schöneck (DE); Elisabeth Defossa, Idstein (DE); Fahad A. Al-Obeidi, Tucson, AZ (US); Armin Walser, Tucson, AZ (US); James Ostrem, Tucson, AZ (US)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/697,188

(22) Filed: Oct. 27, 2000

(30) Foreign Application Priority Data

Oct. 30, 1999 (EP) .............................................. 99121623

(51) Int. Cl.⁷ ...................... C07C 233/05; C07C 233/65
(52) U.S. Cl. ........................ 564/157; 514/357; 514/565; 514/616; 546/332; 562/439; 564/153
(58) Field of Search ................................ 564/157, 153; 514/616, 565; 546/332; 562/439

(56) References Cited

U.S. PATENT DOCUMENTS 5,525,623 A * 6/1996 Spear et al. ................. 514/423
5,616,620 A 4/1997 Rudolf et al.

FOREIGN PATENT DOCUMENTS

| EP | 0 987 274 A1 | 3/2000 |
|---|---|---|
| WO | WO 92/06711 | 4/1992 |
| WO | WO 94/08941 | 4/1994 |
| WO | WO 94/17035 | 8/1994 |
| WO | WO 95/29189 | 11/1995 |
| WO | WO 96/12800 | 5/1996 |
| WO | WO 97/47651 | 12/1997 |
| WO | WO 99/15498 | 4/1999 |
| WO | WO 99/33800 | 7/1999 |
| WO | WO 00/15658 | 3/2000 |

OTHER PUBLICATIONS

Irwin H. Segel, *Enzyme Kinetics*, 1975, John Wiley & Sims, New York, pp. 100–125.
James A. Ostrem, et al., "Discovery of a Novel, Potent, and Specific Family of Factor Xa Inhibitors via Combinatorial Chemistry," *Biochemistry*, 37: 1053–1059 (1998).
Oyo Mitsunobu, "The Use of Diethyl Azodicarboxylate and Triphenylphosphine in Synthesis and Transformation of Natural Products," Synthesis, pp. 1–28 (1981).
Hans Bundgaard, "Novel Chemical Approaches in Prodrug Design," *Drugs of the Future,* 16(5): 443–458 (1991).
Yung–chi Cheng and William H. Prusoff, "Relationship Between the Inhibition Constant ($K_1$) and the Concentration of Inhibitor which Causes 50 Per Cent Inhibition ($I_{50}$) of an Enzymatic Reaction," *Biochemical Pharmacology,* 22: 3099–3108 (1973).
David Fleisher, Ramon Bong and and Barbra H. Stewart, "Improved Oral Drug Delivery: Solubility Limitations Overcome by the Use of Prodrugs," *Advanced Drug Delivery Reviews,* 19: 115–130 (1996).

* cited by examiner

*Primary Examiner*—Shailenora Kumar
(74) *Attorney, Agent, or Firm*—Finnegan, Henderson, Farabow, Garrett & Dunner, L.L.P.

(57) ABSTRACT

The present invention relates to compounds of the formula I,

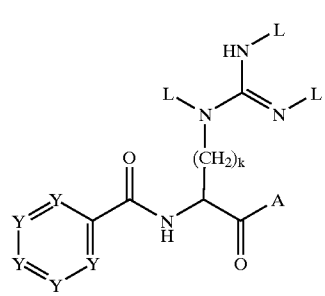

in which A, L, Y, and k have the meanings indicated in the specification and claims. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa and/or factor VIIa and can in general be applied in conditions in which an undesired activity of factor Xa and/or factor VIIa is present or for the cure or prevention of conditions in which an inhibition of factor Xa and/or factor VIIa is intended. The invention furthermore relates to processes for the preparation of compounds of the formula I, their use, in particular active ingredients in pharmaceuticals, and pharmaceutical preparations comprising them.

7 Claims, No Drawings

N-GUANIDINOALKYLAMIDES, THEIR PREPARATION, THEIR USE, AND PHARMACEUTICAL PREPARATIONS COMPRISING THEM

The present invention relates to compounds of the formula I,

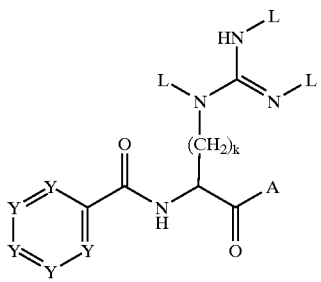

in which A, L, Y, and k are as defined below. Compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VII (FVIIa), and can in general be applied in conditions in which an undesirable activity of factor Xa and/or factor VIIa is present, or for the cure or prevention of conditions in which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

The ability to form blood clots is vital to survival. The formation of a blood clot or a thrombus is normally the result of tissue injury which initiates the coagulation cascade and has the effect of slowing or preventing blood flow in wound healing. Other factors which are not directly related to tissue injury like atherosclerosis and inflammation may also initiate the coagulation cascade. In general, a relationship exists between inflammation and the coagulation cascade. Inflammation mediators regulate the coagulation cascade and coagulation components influence the production and activity of inflammation mediators.

However, in certain disease states the formation of blood clots within the circulatory system reaches an undesired extent and is itself the source of morbidity, potentially leading to pathological consequences. It is nevertheless not desirable in such disease states to completely inhibit the blood clotting system because life threatening hemorrhage would ensue. In the treatment of such states, a finely tuned intervention into the blood clotting system is required, and there is still a need for substances exhibiting a suitable pharmacological activity profile for achieving such a result.

Blood coagulation is a complex process involving a progressively amplified series of enzyme activation reactions in which plasma zymogens are sequentially activated by limited proteolysis. Mechanistically, the blood coagulation cascade has been divided into intrinsic and extrinsic pathways, which converge at the activation of factor X. Subsequent generation of thrombin proceeds through a single common pathway (see Scheme 1). Present evidence suggests that the intrinsic pathway plays an important role in the maintenance and growth of fibrin formation, while the extrinsic pathway is critical in the initiation phase of blood coagulation. It is generally accepted that blood coagulation is physically initiated upon formation of a factor VIIa/tissue factor (TF) complex. Once formed, this complex rapidly initiates coagulation by activating factors IX and X. The newly generated activated factor X, i.e., factor Xa, then forms a one-to-one complex with factor Va and phospholipids to form a prothrombinase complex, which is responsible for converting soluble fibrinogen to insoluble fibrin via the activation of thrombin from its precursor prothrombin.

Scheme 1
Blood coagulation cascade

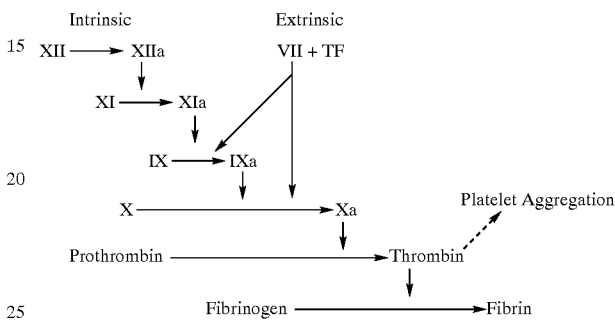

As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor complex. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin. The autocatalytic nature of thrombin generation is an important safeguard against uncontrolled bleeding, ensuring that, once a given threshold level of prothrombinase is present, blood coagulation will proceed to completion. Thus, it is desirable to develop agents that inhibit coagulation without directly inhibiting thrombin but rather by inhibiting other steps in the coagulation cascade, like factor Xa and/or factor VIIa activity.

In many clinical applications, there is a great need for the prevention of intravascular blood clots or for some anticoagulant treatment. For example, nearly 50% of patients who have undergone a total hip replacement develop deep vein thrombosis (DVT). Currently available drugs, like heparin and derivatives thereof, are not satisfactory in many specific clinical applications. The currently approved therapies include fixed dose low molecular weight heparin (LMWH) and variable dose heparin. Even with these drug regimes, 10% to 20% of patients develop DVT, and 5% to 10% develop bleeding complications.

Better anticoagulants are also needed for subjects undergoing transluminal coronary angioplasty and subjects at risk for myocardial infarction or suffering from crescendo angina. The present conventionally accepted therapy of administering heparin and aspirin is associated with a 6% to 8% abrupt vessel closure rate within 24 hours of the procedure. The rate of bleeding complications requiring transfusion therapy due to the use of heparin also is approximately 7%. Moreover, even though delayed closures are significant, administration of heparin after termination of the procedure is of little value and can be detrimental.

Widely used blood clotting inhibitors, such as heparin, and related sulfated polysaccharides such as LMWH and heparin sulfate, exert their anticlotting effects by promoting the binding of a natural regulator of the clotting process, antithrombin III, to thrombin and to factor Xa. The inhibitory activity of heparin primarily is directed toward thrombin, which is inactivated approximately 100 times faster than factor Xa. Hirudin and hirulog are two additional thrombin specific anticoagulants. However, these anticoagulants which inhibit thrombin are also associated with bleeding complications. Preclinical studies in baboons and dogs have shown that targeting enzymes involved at earlier stages of the coagulation cascade, such as factor Xa or factor VIIa, prevents clot formation without producing the bleeding side effects observed with direct thrombin inhibition.

Several specific inhibitors of factor Xa have been reported. Both synthetic and protein inhibitors of factor Xa have been identified, these include, for example, antistasin (ATS) and tick anticoagulant peptide (TAP). ATS, which is isolated from the leech, *Haementerin officinalis*, contains 119 amino acids and has a $K_i$ for factor Xa of 0.05 nM. TAP, which is isolated from the tick, *Ornithodoros moubata*, contains 60 amino acids and has a $K_i$ for factor Xa of about 0.5 nM.

The effectiveness of recombinantly produced ATS and TAP have been investigated in a number of animal model systems. Both inhibitors decrease bleeding time compared to other anticoagulants, and prevent clotting in a thromboplastin induced, ligated jugular vein model of deep vein thrombosis. The results achieved in this model correlate with results obtained using the current drug of choice, heparin.

Subcutaneous ATS also was found to be an effective treatment in a thromboplastin induced model of disseminated intravascular coagulation (DIC). TAP effectively prevents "high shear" arterial thrombosis and "reduced flow" caused by the surgical placement of a polyester (DACRON) graft at levels that produced a clinically acceptable prolongation of the activated partial thromboplastin time (aPTT), i.e., less than about two fold prolongation. By comparison, standard heparin, even at doses causing a five fold increase in the aPTT, did not prevent thrombosis and reduced flow within the graft. The aPTT is a clinical assay of coagulation which is particularly sensitive to thrombin inhibitors.

ATS and TAP have not been developed clinically. One major disadvantage of these two inhibitors is that administration of the required repeated doses causes the generation of neutralizing antibodies, thus limiting their potential clinical use.

Moreover, the sizes of TAP and ATS render oral administration impossible, further restricting the number of patients able to benefit from these agents. An inhibitor of factor Xa with a favorable property profile would have substantial practical value in the practice of medicine. In particular, a factor Xa inhibitor would be effective under circumstances where the present drugs of choice, like heparin and related sulfated polysaccharides, are ineffective or only marginally effective.

Low molecular weight, factor Xa-specific blood clotting inhibitors that are effective but do not cause unwanted side effects have been described, for example, in WO-A-95/29189. Indole derivatives as low molecular weight factor Xa-specific blood clotting inhibitors have been disclosed in WO-A-99/33800. However, besides being an effective factor Xa-specific blood clotting inhibitor, such inhibitors should also have further advantageous properties, for instance, high stability in plasma and liver, high selectivity versus other serine proteases whose inhibition is not intended, such as thrombin, or inhibitory activity against serine proteases whose inhibition is desired, such as factor VIIa. There is-an ongoing need in the art for further low molecular weight factor Xa specific blood clotting inhibitors which are effective and have the above advantages as well.

Specific inhibition of the factor VIIa/tissue factor catalytic complex using monoclonal antibodies (WO-A-92/06711), or using a protein such as chloromethyl ketone inactivated factor VIIa (WO-A-96/12800, WO-A-97/7651) is an extremely effective means of controlling thrombus formation caused by acute arterial injury or by the thrombotic complications related to bacterial septicemia. There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. For example, WO-A-00/15658 (corresponding to EP-A-987274 (application no. 98117506.0)) discloses compounds containing a tripeptide unit which inhibit factor VIIa. However, the property profile of these compounds is still not ideal, and an ongoing need in the art exists for further low molecular weight factor VIIa inhibitory blood clotting inhibitors.

The present invention satisfies the above needs by providing novel compounds of the formula I which exhibit factor Xa and/or factor VIIa inhibitory activity and which are favorable agents for inhibiting unwanted blood clotting and thrombus formation.

Thus, the present invention relates to compounds of the formula I,

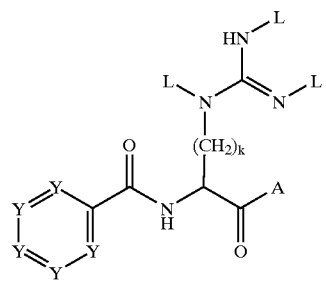

I wherein
one or two of the Y groups are carbon atoms bonded to a group of the formula II,

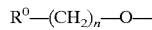

II zero, one, two, or three of the Y groups are nitrogen atoms, and the remaining Y groups are carbon atoms bonded to $R^1$ as defined below, where the Y groups are independent of each other and can be identical or different;

L is selected from hydrogen, $(C_1-C_8)$-alkylcarbonyl, $(C_6-C_{14})$-aryl-$(C_1-C_4)$-alkylcarbonyl, $(C_6-C_{14})$-arylcarbonyl, $(C_1-C_8)$-alkyloxycarbonyl, $(C_6-C_{14})$-aryl-$(C_1-C_4)$-alkyloxycarbonyl, and $(C_6-C_{14})$-aryloxycarbonyl, wherein any aryl group or groups in L are unsubstituted, or substituted by one or more identical or different substituents $R^{13}$, and where the L groups are selected independently of one another and are identical or different;

A is selected from $R^3O$— and $R^4R^5N$—;

k is 1, 2, 3, or 4;

n is 0, 1, 2, 3, or 4;

$R^0$ is selected from phenyl, and monocyclic 6-membered heteroaryl containing one or two nitrogen atoms as ring heteroatoms, wherein $R^0$ is unsubstituted, or substituted by one or more identical or different $R^2$ groups defined as follows;

$R^1$ is selected from hydrogen, halogen, nitro, hydroxy, $(C_1-C_8)$-alkyloxy-, $(C_6-C_{14})$-aryl, $(C_1-C_8)$-alkyl, hydroxycarbonyl-$(C_1-C_8)$-alkylureido-, $(C_1-C_8)$-alkyloxycarbonyl-$(C_1-C_8)$-alkylureido-, $(C_1-C_8)$-alkylsulfonyl-, and $R^{11}R^{12}N$—, where $R^1$ is selected independently of each other and can be identical or different, and where alkyl and aryl groups present in $R^1$ are unsubstituted, or substituted by one or more identical or different substituents $R^{13}$, or two $R^1$ groups, bonded to adjacent ring carbon atoms, together with the carbon atoms to which they are bonded, form an aromatic ring fused to the ring depicted in formula I, where the ring thereby formed is unsubstituted or substituted by one or more identical or different substituents $R^{13}$ defined as follows;

$R^2$ is selected from halogen, nitro, $(C_1-C_8)$-alkyl, cyano, hydroxy, amino, and $(C_1-C_8)$-alkyloxy-, wherein any alkyl group or groups present in $R^2$ are unsubstituted, or substituted by one or more identical or different halogen atoms;

$R^3$, $R^4$, and $R^5$ are selected from hydrogen, $(C_1-C_{12})$-alkyl, $(C_6-C_{14})$-aryl-$(C_1-C_4)$-alkyl-, $(C_6-C_{14})$-aryl-, Het-, and Het-$(C_1-C_4)$-alkyl-, where $R^4$ and $R^5$ are selected independently of one another and can be identical or different, and wherein the groups alkyl, aryl, and Het present in $R^3$, $R^4$, and $R^5$ are unsubstituted, or substituted by one or more identical or different substituents $R^{13}$ defined as follows, or $R^4$ and $R^5$, together with the nitrogen atom to which they are bonded, form a saturated 3-membered to 8-membered monocyclic heterocyclic ring which, in addition to the nitrogen atom bound to $R^4$ and $R^5$, optionally contains one or two identical or different ring heteroatoms selected from oxygen, sulfur, and nitrogen;

$R^{11}$ and $R^{12}$, which are selected independently of each other, and are identical or different, are selected from hydrogen, $(C_1-C_8)$-alkyl, $(C_6-C_{14})$-aryl-$(C_1-C_4)$-alkyl-, Het-$(C_1-C_4)$-alkyl-, hydroxycarbonyl-$(C_1-C_8)$-alkyl-, $(C_1-C_8)$-alkyloxycarbonyl-$(C_1-C_8)$-alkyl-, hydroxycarbonyl-$(C_1-C_8)$-alkylcarbonyl-, $(C_1-C_8)$-alkyloxycarbonyl-$(C_1-C_8)$-alkylcarbonyl-, and $(C_1-C_8)$-alkylcarbonyl-, wherein any alkyl and/or aryl groups present in $R^{11}$ and $R^{12}$ are unsubstituted, or substituted by one or more identical or different substituents $R^{13}$ defined as follows, or $R^{11}$ and $R^{12}$, together with the nitrogen atom to which they are bonded, form a saturated or unsaturated 5-membered to 8-membered monocyclic heterocyclic ring, which, in addition to the nitrogen atom bound to $R^{11}$ and $R^{12}$, optionally contains one or two identical or different ring heteroatoms selected from oxygen, sulfur, and nitrogen, and in which one or two of the ring carbon atoms is optionally substituted by oxo to form C=O group(s);

$R^{13}$ is selected from halogen, nitro, cyano, hydroxy, $(C_1-C_8)$-alkyl, $(C_1-C_8)$-alkyloxy, trifluoromethyl, and amino; and Het is a residue of a saturated, partially unsaturated, or aromatic monocyclic or bicyclic, 3-membered to 10-membered heterocyclic ring system containing one, two, three or four identical or different heteroatoms selected from nitrogen, oxygen, and sulfur;

in all their stereoisomeric forms and mixtures thereof in any ratio, and their physiologically tolerable salts.

In general, the meaning of any group, residue, heteroatom, number, etc. which can occur more than once in the compounds of formula I, is selected independently of the meaning of this group, residue, heteroatom, number etc. in any other occurrence. All groups, residues, heteroatoms, numbers, etc. which can occur more than once in the compounds of formula I can be identical or different. For example, in case that a compound of the formula I contains two groups of the formula II, they can be identical or different with respect to the number n and/or the group $R^0$.

As used herein, the term alkyl is to be understood in the broadest sense to mean hydrocarbon residues which can be linear, i.e., straight-chain, or branched, and which can be acyclic or cyclic, or any combination of acyclic and cyclic subunits. Further, the term alkyl as used herein expressly includes saturated groups as well as unsaturated groups. Unsaturated groups contain one or more, for example, one, two, or three, double bonds and/or triple bonds, provided that the double bonds are not located within a cyclic alkyl group in such a manner that an aromatic system results. All these statements also apply if an alkyl group occurs as a substituent on or in another residue, for example, in an alkyloxy residue, an alkyloxycarbonyl residue or an arylalkyl residue. Examples of alkyl residues containing 1, 2, 3, 4, 5, 6, 7, 8, 9, 10, 11, or 12 carbon atoms are methyl, ethyl, propyl, butyl, pentyl, hexyl, heptyl, octyl, nonyl, decyl, undecyl, dodecyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-butyl, tert-pentyl, 2,3,4-trimethylhexyl, and isodecyl.

Examples of unsaturated alkyl residues are alkenyl residues such as vinyl, 1-propenyl, 2-propenyl (=allyl), 2-butenyl, 3-butenyl, 2-methyl-2-butenyl, 3-methyl-2-butenyl, 5-hexenyl, and 1,3-pentadienyl, or alkynyl residues such as ethynyl, 1-propynyl, 2-propynyl (=propargyl), and 2-butynyl. Alkyl residues can also be unsaturated when they are substituted.

Examples of cyclic alkyl residues are cycloalkyl residues containing 3, 4, 5, 6, 7 or 8 ring carbon atoms such as cyclopropyl, cyclobutyl, cyclopentyl, cyclohexyl, cycloheptyl, or cyclooctyl, any of which can be optionally substituted and/or unsaturated. Unsaturated cyclic alkyl groups and unsaturated cycloalkyl groups, such as cyclopentenyl or cyclohexenyl, can be bonded via any carbon atom. The term alkyl as used herein also comprises cycloalkyl-substituted alkyl groups such as cyclopropylmethyl-, cyclobutylmethyl-, cyclopentylmethyl-, cyclohexylmethyl-, cycloheptylmethyl-, 1-cyclopropylethyl-, 1-cyclobutylethyl-, 1-cyclopentylethyl-, 1-cyclohexylethyl-, 2-cyclopropylethyl-, 2-cyclobutylethyl-, 2-cyclopentylethyl-, 2-cyclohexylethyl-, 3-cyclopropylpropyl-, 3-cyclobutylpropyl-, 3-cyclopentylpropyl, etc., wherein the cycloalkyl subgroup as well as the acyclic subgroup can be optionally unsaturated and/or substituted.

Of course, a cyclic alkyl group must contain at least three carbon atoms, and an unsaturated alkyl group must contain at least two carbon atoms. Thus, a group like $(C_1-C_8)$-alkyl is to be understood as comprising, among others, saturated acyclic $(C_1–C_8)$-alkyl, $(C_3–C_8)$-cycloalkyl, cycloalkyl-alkyl groups like $(C_3–C_7)$-cycloalkyl-$(C_1–C_5)$-alkyl-, wherein the total number of carbon atoms can range from 4 to 8, and unsaturated $(C_2–C_8)$-alkyl, such as $(C_2–C_8)$-alkenyl or $(C_2–C_8)$-alkynyl. Similarly, a group like $(C_1–C_4)$-alkyl is to be understood as comprising, among others, saturated acyclic $(C_1–C_4)$-alkyl, $(C_3–C_4)$-cycloalkyl, cyclopropylmethyl-, and unsaturated $(C_2–C_4)$-alkyl, such as $(C_2–C_4)$-alkenyl or $(C_2–C_4)$-alkynyl.

In one embodiment of the present invention, the term alkyl comprises acyclic saturated hydrocarbon residues which can be linear or branched. In another embodiment, the term alkyl comprises acyclic saturated hydrocarbon residues having from one to six carbon atoms. One group of saturated acyclic alkyl residues of interest is $(C_1–C_4)$-alkyl residues, such as methyl, ethyl, n-propyl, isopropyl, n-butyl, isobutyl, sec-butyl, and tert-butyl.

Unless stated otherwise, and irrespective of any specific substituents bonded to alkyl groups which are indicated in the definition of the compounds of the formula I, alkyl groups can be unsubstituted, or substituted by one or more, for example, one, two, three, four, or five, identical or different substituents. Any kind of substituents present in substituted alkyl residues can be present in any desired position, provided that the substitution does not lead to an unstable molecule. Examples of substituted alkyl residues are alkyl residues in which one or more, for example, 1, 2, 3, 4, or 5, hydrogen atoms are replaced with halogen atoms. In one embodiment of the present invention, the halogen atoms in halogen-substituted alkyl residues are fluorine atoms.

The term aryl refers to a monocyclic or polycyclic hydrocarbon residue wherein at least one carbocyclic ring is present with a conjugated pi electron system. In a $(C_6–C_{14})$-aryl residue, from 6 to 14 ring carbon atoms are present. Examples of $(C_6–C_{14})$-aryl residues are phenyl, naphthyl, biphenylyl, fluorenyl, and anthracenyl. Examples of $(C_6–C_{10})$-aryl residues are phenyl and naphthyl. Unless stated otherwise, and irrespective of any specific substituents bonded to aryl groups which are indicated in the definition of the compounds of the formula I, aryl residues, such as phenyl, naphthyl, or fluorenyl, can be unsubstituted, or substituted by one or more, for example, one, two, three, or four, identical or different substituents. Aryl residues can be bonded via any position, and in substituted aryl residues, substituents can be located in any position.

Unless stated otherwise, and irrespective of any specific substituents bonded to aryl groups which are indicated in the definition of the compounds of the formula I, substituents optionally present in substituted aryl groups are, for example, $(C_1–C_8)$-alkyl, such as $(C_1–C_4)$-alkyl (e.g., methyl, ethyl or tert-butyl), hydroxy, $(C_1–C_8)$-alkyloxy, such as $(C_1–C_4)$-alkyloxy (e.g., methoxy, ethoxy or tert-butoxy), methylenedioxy, ethylenedioxy, F, Cl, Br, I, cyano, nitro, trifluoromethyl, trifluoromethoxy, hydroxymethyl, formyl, acetyl, amino, mono- or di-$(C_1–C_4)$-alkylamino, $((C_1–C_4)$-alkyl)carbonylamino (such as acetylamino), hydroxycarbonyl, $((C_1–C_4)$-alkyloxy)carbonyl, carbamoyl, optionally substituted phenyl, benzyl optionally substituted in the aromatic group, optionally substituted phenoxy or benzyloxy optionally substituted in the aromatic group. A substituted aryl group that can be present in a specific position of the compounds of formula I can, independently of other aryl groups, be substituted by substituents selected from any desired subgroup of the substituents listed before and/or in the specific definition of that group. For example, a substituted aryl group may be substituted by one or more identical or different substituents selected from $(C_1–C_4)$-alkyl, hydroxy, $(C_1–C_4)$-alkyloxy, F, Cl, Br, I, cyano, nitro, trifluoromethyl, amino, phenyl, benzyl, phenoxy, and benzyloxy. One embodiment of the invention is compounds of the formula I where not more than two nitro groups are present.

In monosubstituted phenyl residues, the substituent can be located in the 2-position, the 3-position, or the 4-position. In one embodiment of the present invention, the substituent in monosubstituted phenyl residues is located in the 3-position or the 4-position. If a phenyl group has two substituents, they can be located in 2,3-position, 2,4-position, 2,5-position, 2,6-position, 3,4-position, or 3,5-position. In phenyl residues having three substituents, the substituents can be located in 2,3,4-position, 2,3,5-position, 2,3,6-position, 2,4,5-position, 2,4,6-position, or 3,4,5-position.

Naphthyl residues can be 1-naphthyl or 2-naphthyl. In substituted naphthyl residues, the substituent(s) can be located in any position(s), for example, in monosubstituted 1-naphthyl residues in the 2-, 3-, 4-, 5-, 6-, 7-, or 8-position, and in monosubstituted 2-naphthyl residues in the 1-, 3-, 4-, 5-, 6-, 7-, or 8-position. Biphenylyl residues can be 2-biphenylyl, 3-biphenylyl, and 4-biphenylyl. Fluorenyl residues can be 1-, 2-, 3-, 4-, or 9-fluorenyl. In on embodiment of the present invention, monosubstituted fluorenyl residues bonded via the 9-position have a substituent in the 1-, 2-, 3-, or 4-position.

The above statements relating to aryl groups correspondingly apply to the aryl subgroup in arylalkyl- groups. Examples of arylalkyl- groups, which can also be unsubstituted, or substituted in the aryl subgroup as well as in the alkyl subgroup, are benzyl, 1-phenylethyl, 2-phenylethyl, 3-phenylpropyl, 4-phenylbutyl, 1-methyl-3-phenyl-propyl, 1-naphthylmethyl, 2-naphthylmethyl, 1-(1-naphthyl)ethyl, 1-(2-naphthyl)ethyl, 2-(1-naphthyl)ethyl, 2-(2-naphthyl)ethyl, and 9-fluorenylmethyl.

The Het group comprises groups containing 3, 4, 5, 6, 7, 8, 9, or 10 ring atoms in the parent monocyclic or bicyclic heterocyclic ring system. In Het monocyclic groups, the heterocyclic ring preferably is a 3-membered, 4-membered, 5-membered, 6-membered or 7-membered ring. In one embodiment of the present invention, monocyclic Het groups are 5-membered or 6-membered rings. In bicyclic groups, Het is preferably two fused rings, one of which is a 5-membered ring or 6-membered heterocyclic ring and the other of which is a 5-membered or 6-membered heterocyclic or carbocyclic ring, e.g., a bicyclic ring Het may contain 8, 9, or 10 ring atoms. In one embodiment of the present invention, bicyclic Het groups contain 9 or ring atoms.

Het comprises saturated heterocyclic ring systems which do not contain any double bonds within the rings, as well as mono-unsaturated and poly-unsaturated heterocyclic ring systems which contain one or more, for example, one, two, three, four, or five, double bonds within the rings, provided that the resulting system is stable. Unsaturated rings may be non-aromatic or aromatic, i.e., double bonds within the rings in the Het group may or may not be arranged in such a manner that a conjugated pi electron system results. Aromatic rings in a Het group may be 5-membered or 6-membered rings, i.e., aromatic groups in a Het group contain 5 to 10 ring atoms. Aromatic rings in a Het group thus comprise 5-membered and 6-membered monocyclic heterocycles and bicyclic heterocycles composed of two 5-membered rings, one 5-membered ring and one 6-membered ring, or two 6-membered rings. In bicyclic aromatic groups in a Het group, one or both rings may contain heteroatoms. Aromatic Het groups may also be referred to by the customary term heteroaryl for which all the definitions and explanations above and below relating to Het correspondingly apply.

Unless stated otherwise, in the Het groups and in any other heterocyclic groups, one embodiment of interest is groups with 1, 2, 3, or 4 identical or different ring heteroatoms selected from nitrogen, oxygen, and sulfur. Another embodiment has hetererocyclic groups wherein one or two identical or different heteroatoms are selected from nitrogen, oxygen, and sulfur. The ring heteroatoms can be present in any desired number and in any position with respect to each other, provided that the resulting heterocyclic system is known in the art, is stable, and is suitable as a subgroup in a drug substance. Examples of parent structures of heterocycles from which the Het group is optionally derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, pteridine etc., as well as ring systems which result from the listed heterocycles by fusion (or condensation) of a carbocyclic ring, for example, benzo-fused, cyclopenta-fused, cyclohexa-fused or cyclohepta-fused derivatives of these heterocycles.

The fact that many of the before-listed names of heterocycles are the chemical names of unsaturated or aromatic ring systems does not imply that the Het groups could only be derived from the respective unsaturated ring system. The names here only serve to describe the ring system with respect to ring size and the number of the heteroatoms and their relative positions. As explained above, the Het group can be saturated or partially unsaturated or aromatic, and can thus be derived not only from the before-listed heterocycles themselves but also from all their partially or completely hydrogenated analogues and also from their more highly unsaturated analogues if applicable. Some examples of completely or partially hydrogenated analogues of the before-listed heterocycles from which the groups Het are optionally derived are following: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The residue Het may be bonded via any ring carbon atom, and, in the case of nitrogen heterocycles, via any suitable ring nitrogen atom. Thus, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol4-yl or 1,3-oxazol-5-yl, 1,3-thiazolyl can be 1,3-thiazol-2-yl, 1,3-thiazol4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin 4-yl=piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazolyl residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to Het groups or any other heterocyclic groups which are indicated in the definition of the compounds of the formula I, the Het group can be unsubstituted, or substituted on ring carbon atoms with one or more, for example, one, two, three, four, or five, identical or different substituents such as $(C_1-C_8)$-alkyl (such as $(C_1-C_4)$-alkyl), $(C_1-C_8)$-alkyloxy (such as $(C_1-C_4)$-alkyloxy), $(C_1-C_4)$-alkylthio, halogen, nitro, amino, $((C_1-C_4)$-alkyl) carbonylamino (such as acetylamino), trifluoromethyl, trifluoromethoxy, hydroxy, oxo, hydroxy-$(C_1-C_4)$-alkyl (such as hydroxymethyl, 1-hydroxyethyl, or 2-hydroxyethyl), methylenedioxy, ethylenedioxy, formyl, acetyl, cyano, methylsulfonyl, hydroxycarbonyl, aminocarbonyl, $(C_1-C_4)$-alkyloxycarbonyl, optionally substituted phenyl, optionally substituted phenoxy, benzyl optionally substituted in the aromatic group, benzyloxy optionally substituted in the aromatic group, etc. The substituents can be present in any desired position, provided that a stable molecule results. Of course, an oxo group cannot be present in an aromatic ring. Each suitable ring nitrogen atom in a Het group can independently of each other be unsubstituted, e.g., carry a hydrogen atom, or can be substituted, e.g., carry a substituent like $(C_1-C_8)$-alkyl (for example, $(C_1-C_4)$-alkyl such as methyl or ethyl), optionally substituted phenyl, phenyl-$(C_1-C_4)$-alkyl, (such as benzyl optionally substituted in the aromatic group), hydroxy-$(C_2-C_4)$-alkyl (such as 2-hydroxyethyl), acetyl or another acyl group, methylsulfonyl or another sulfonyl group, aminocarbonyl, $(C_1-C_4)$-alkyloxycarbonyl, etc. In general, in the compounds of the formula I, nitrogen heterocycles are optionally present as N-oxides or as quaternary salts. Ring sulfur atoms can be oxidized to the sulfoxide or to the sulfone. Thus, a tetrahydrothienyl residue may be present as S,S-dioxotetrahydrothienyl residue, or a thiomorpholinyl residue like thiomorpholin-4-yl may be present as 1-oxo-thiomorpholin-4-yl or 1,1-dioxo-thiomorpholin-4-yl. A substituted Het group that can be present in a specific position of the compounds of formula I can independently of other Het groups be substituted by substituents selected from any desired subgroup of the substituents listed before and/or in the definition of that group.

The above statements relating to the Het group also correspondingly apply to the Het subgroup in the groups Het-alkyl-. Examples of such Het-alkyl-groups which can also be unsubstituted or substituted in the Het subgroup as well as optionally substituted in the alkyl subgroup, are (pyridin-2-yl)-methyl, (pyridin-3-yl)-methyl, (pyridin-4-yl)- methyl, 2-(pyridin-2-yl)-ethyl, 2-(pyridin-3-yl)-ethyl, or 2-(pyridin-4-yl)-ethyl. As far as applicable, the above statements relating to the Het group also apply to the heteroaryl group in $R^0$, and to a heterocyclic ring that is formed by two groups together with the nitrogen atom to which they are bonded.

In one embodiment of the present invention, halogen is fluorine, chlorine, bromine, or iodine. In another embodiment, halogen is fluorine, chlorine, or bromine. Still another embodiment comprises compounds where halogen is chlorine or bromine.

Optically active carbon atoms present in the compounds of the formula I can, independently of one another, have R configuration or S configuration. The compounds of formula I can be present in the form of pure or substantially pure enantiomers, or pure or substantially pure diastereomers, or in the form of mixtures of enantiomers and/or diastereomers, for example, in the form of racemates. The present invention relates to pure enantiomers and mixtures of enantiomers, as well as to pure diastereomers and mixtures of diastereomers. The invention comprises mixtures of two, or of more than two, stereoisomers of the formula I, and it comprises all ratios of the stereoisomers in the mixtures. Where the compounds of the formula I can be present as E isomers or Z isomers (or cis isomers or trans isomers), the invention relates both to pure E isomers, and pure Z isomers, and to E/Z mixtures in all ratios. The invention also comprises all possible tautomeric forms of the compounds of formula I.

Diastereomers, including E/Z isomers, are optionally separated into the individual isomers by chromatography, for example. Racemates can be separated into the two constituent enantiomers by customary methods, for example, by chromatography on chiral phases or by resolution, for example, by crystallization of diastereomeric salts obtained with optically active acids or bases. Stereochemically uniform compounds of the formula I are also optionally obtained by employing stereochemically uniform starting materials or by using stereoselective reactions.

The choice of incorporating into a compound of the formula I a building block with R configuration or S configuration, or in the case of an amino acid unit present in a compound of formula I, of incorporating a building block designated as D-amino acid or L-amino acid, can depend, for example, on the desired characteristics of the compound of formula I. For example, the incorporation of a D-amino acid building block can confer increased stability in vitro or in vivo. Incorporation of a D-amino acid building block also can achieve a desired increase or decrease in the pharmacological activity of the compound. In some cases, it can be desirable to allow the compound to remain active for only a short period of time. In such cases, incorporation of an L-amino acid building block in the compound can allow endogenous peptidases in an individual to digest the compound in vivo, thereby limiting the individual's exposure to the active compound. A similar effect may also be obtained in the compounds of the invention by changing the configuration in another building block from S configuration to R configuration, or vice versa. By taking medical needs into consideration, a person skilled in the art can fine tune desirable characteristics, for example, a favorable stereochemistry, of the required compound of the invention.

Physiologically tolerable salts of the compounds of formula I are nontoxic salts that are physiologically acceptable, e.g., pharmaceutically utilizable salts. Such salts of compounds of formula I containing acidic groups, for example, a carboxy group COOH, are, for example, alkali metal salts or alkaline earth metal salts such as sodium salts, potassium salts, magnesium salts and calcium salts, and also salts with physiologically tolerable quarternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl) amine. Basic groups contained in the compounds of formula I, for example, amino groups or guanidino groups, form acid addition salts, for example, with inorganic acids such as hydrochloric acid, hydrobromic acid, sulfuric acid, nitric acid, or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid, or p-toluenesulfonic acid. Compounds of the formula I which simultaneously contain a basic group and an acidic group, for example, a guanidino group and a carboxy group, can also be present as zwitterion (betaines) which are likewise included in the present invention.

Salts of compounds of the formula I can be obtained by customary methods known to those skilled in the art, for example, by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example, hydrates or adducts with alcohols. The invention also includes derivatives and modifications of the compounds of the formula I, for example, prodrugs, protected forms and other physiologically tolerable derivatives including esters and amides, as well as active metabolites of the compounds of the formula I. Such esters and amides are, for example, $(C_1–C_4)$-alkyl esters, unsubstituted amides, or $(C_1–C_8)$-alkylamides. Embodiments of the current invention are prodrugs and protected forms of the compounds of the formula I which can be converted into compounds of the formula I under physiological conditions. Suitable prodrugs for the compounds of the formula I, e.g., chemically modified derivatives of the compounds of the formula I having properties which are improved in a desired manner, for example, with respect to solubility, bioavailability, or duration of action, are known to those skilled in the art. More detailed information relating to prodrugs is found in standard literature, such as *Design of Prodrugs,* H. Bundgaard (ed.), Elsevier (1985); D. Fleisher et al., *Advanced Drug Delivery Reviews* 19 (1996) 115–130; or H. Bundgaard, *Drugs of the Future* 16 (1991) 443; which are all incorporated herein by reference. Suitable prodrugs for the compounds of the formula I are especially ester prodrugs and amide prodrugs of carboxylic acid groups, and also acyl prodrugs and carbamate prodrugs of acylatable nitrogen-containing groups such as amino groups and guanidino groups. In the acyl prodrugs and carbamate prodrugs one or more, for example, one or two, hydrogen atoms on nitrogen atoms in such groups are replaced with an acyl group or a carbamate group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1–C_{18})$-alkyl, $(C_3–C_8)$-cycloalkyl, $(C_3–C_8)$-cycloalkyl- ($C_1$–$C_4$)-alkyl-, ($C_6$–$C_{14}$)-aryl, Het-, ($C_6$–$C_{14}$)-aryl-($C_1$–$C_4$)-alkyl-, or Het-($C_1$–$C_4$)-alkyl- and in which $R^{P2}$ has the meanings indicated for $R^{P1}$ with the exception of hydrogen.

A specific subgroup of compounds of the present invention is formed by compounds in which A is $R^4R^5N$—, and another specific subgroup of compounds of the present invention is formed by compounds in which A is $R^3O$—. Independently thereof, a specific subgroup of compounds of the present invention is formed by compounds in which L is hydrogen, and another specific subgroup is formed by compounds in which one or more of the L groups are acyl groups, for example, acyl groups selected from the acyl L groups listed in the above definition of L, or chosen from any combination of the listed acyl groups. If an aryl group present in an L group is substituted, it is substituted by one, two, three, or four, particularly by one or two, identical or different substituents. If L groups in the compounds of the formula I are different from hydrogen, preferably only one or two of the L groups are different from hydrogen.

The integer k preferably is 2, 3, or 4, more preferably 3. In one embodiment of the invention, the optically active carbon atom depicted in the formula I which carries the groups —C(=O)—A and —(CH$_2$)$_k$—N(L)—C(=N—L)—NHL is present in a uniform configuration or substantially uniform configuration, such as in S configuration or substantially in S configuration.

In the aromatic ring system depicted in the formula I formed by the five Y groups and the ring carbon atom carrying the amide group, the one or two ring carbon atoms carrying the groups of the formula II and any ring nitrogen atoms can be present in any combination and in any positions provided that the resulting system is stable and suitable as a subgroup in a drug substance. One embodiment of the invention encompasses compounds where the aromatic ring system has zero, one, or two of the Y groups as nitrogen atoms. Examples of parent structures from which the aromatic ring system can be derived are benzene, pyridine, pyridazine, pyrimidine, pyrazine, 1,2,3-triazine, 1,2,4-triazine, and 1,3,5-triazine. Another embodiment is where the aromatic ring system is derived from benzene, pyridine, or pyrimidine, and a further embodiment is where the aromatic ring system is derived from benzene.

If zero ring nitrogen atoms are present in the aromatic ring depicted in formula I, instead of the CY$_5$—C(=O)—NH— moiety the compounds of the formula I specifically contain a benzamide moiety of the formula IIIa:

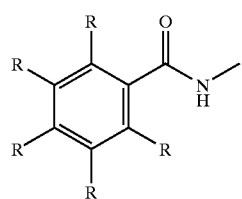

IIIa in which one or two of the R groups are identical or different groups of the formula II and the remaining of the R groups are identical or different $R^1$ groups.

If one ring nitrogen atom is present in the aromatic ring system of formula I, it can be present in a 2-position or a 3-position or in the 4-position with respect to the ring carbon atom carrying the amide group C(=O)—NH depicted in the formula I. For example, if one ring nitrogen atom is present, instead of the CY$_5$—C(=O)—NH— moiety, the compounds of the formula I specifically contain a pyridine-2-carboxamide moiety of the formula IIIb, a pyridine-3-carboxamide moiety of the formula IIIc, or a pyridine-4-carboxamide moiety of the formula IIId:

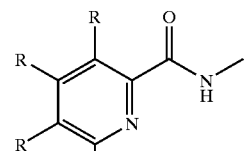

IIIb

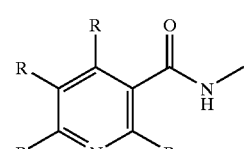

IIIc

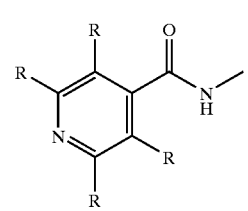

IIId in all of which one or two of the R groups are identical or different groups of the formula II, and the remaining R groups are selected from identical or different $R^1$ groups. Compounds where one ring nitrogen atom is present, and the CY$_5$—C(=O)—NH— moiety is a pyridine-2-carboxamide moiety of the formula IIIb or is a pyridine-4-carboxamide moiety of the formula IIId represent one embodiment of the present invention.

If two ring nitrogen atoms are present in the aromatic ring system in formula I, they can be present in positions 2 and 3, or in positions 2 and 4, or in positions 2 and 5, or in positions 2 and 6, or in positions 3 and 4, or in positions 3 and 5 with respect to the ring carbon atom carrying the amide group C(=O)—NH in the formula I. For example, if two ring nitrogen atoms are present, instead of the CY$_5$—C(=O)—NH— moiety, the compounds of the formula I specifically contain a pyridazine-3-carboxamide moiety of the formula IIIe, a pyridazine-4-carboxamide moiety of the formula IIIf, a pyrimidine-2-carboxamide moiety of the formula IIIg, a pyrimidine-4-carboxamide moiety of the formula IIIh, a pyrimidine-5-carboxamide moiety of the formula IIIi, or a pyrazine-2-carboxamide moiety of the formula IIIj:

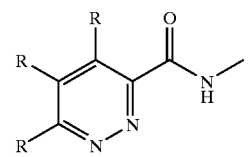

IIIe

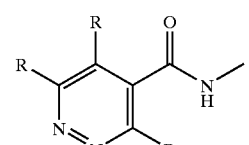

IIIf

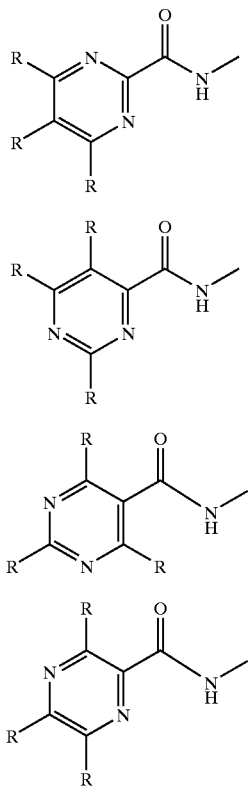

IIIg

IIIh

IIIi

IIIj in all of which one or two of the R groups are identical or different groups of the formula II, and the remaining R groups are selected from identical or different R¹ groups. In case two ring nitrogen atoms are present, the CY₅—C (=O)—NH— moiety may be a pyrimidinecarboxamide moiety of the formulae IIIg, IIIh, or III, e.g., a pyrimidine-4-carboxamide moiety of the formula IIIh. The preceding explanations correspondingly apply to aromatic ring systems in which three ring nitrogen atoms are present.

In general, any one or two of the Y groups in the aromatic ring of formula I which are not nitrogen atoms can be carbon atoms bonded to a group of the formula II. Thus, if one Y group is a carbon atom bonded to a group of the formula II, the group of the formula II can be present in a 2-position or in a 3-position or in the 4-position with respect to the ring carbon atom carrying the amide group C(=O)—NH in the formula I. If only one Y group is a carbon atom carrying a group of the formula II, in one embodiment of the present invention, the group of the formula II is present in the 3-position or in the 4-position with respect to the carbon atom carrying the amide group C(=O)—NH of formula I, especially in the 3-position with respect to said carbon atom. If two Y groups are carbon atoms carrying a group of the formula II, the groups of the formula II can be present in positions 2 and 3, positions 2 and 4, positions 2 and 5, positions 2 and 6, positions 3 and 4 or positions 3 and 5 with respect to the ring carbon atom bonded to the amide group C(=O)—NH of formula I. If two Y groups are carbon atoms bonded to a group of the formula II, it is of particular interest where one or both of the groups of the formula II are present in positions 3, 4, and 5 with respect to the carbon atom carrying the amide group C(=O)—NH of formula I, especially when the two groups of the formula II are present in positions 3 and 4 or positions 3 and 5 with respect to said carbon atom.

For example, if the compound of the formula I contains a benzamide moiety of the formula IIIa and only one Y group is a carbon atom carrying a group of the formula II, the compound of the formula I can contain a benzamide moiety of the formula IIIa-1, or a benzamide moiety of the formula IIIa-2, or a benzamide moiety of the formula IIIa-3:

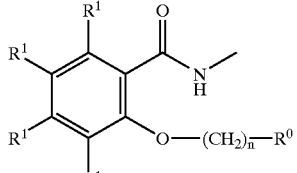

IIIa-1

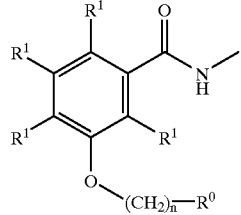

IIIa-2

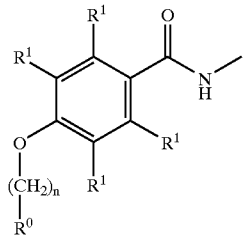

IIIa-3 in all of which R⁰, R¹ and n are defined as above, and of which the benzamide moieties of the formulae IIIa-2 and IIIa-3 are one embodiment of the present invention. Another embodiment of the present invention are compounds of the formula IIIa-2.

Accordingly, if the compound of the formula I contains a pyridinecarboxamide moiety and only one Y group is a carbon atom carrying a group of the formula II, in case of a pyridine-2-carboxamide moiety of the formula IIIb, the group of the formula II can be present in the 3-position or the 4-position or the 5-position or the 6-position with respect to the ring nitrogen atom in the 1-position. An embodiment of interest in this case is where the group of the formula II is in the 4-position, 5-position, or 6-position, and another embodiment is where the group of the formula II is in the 4-position or the 6-position. In case of a pyridine-3-carboxamide moiety of the formula IIIc, the group of the formula II can be present in the 2-position, or the 4-position, or the 5-position, or the 6-position with respect to the ring nitrogen atom in the 1-position, with the 5-position and 6-position being of special interest, and the 5-position being of particular interest. In case of a pyridine-4-carboxamide moiety of the formula IIIid, the group of the formula II can be present in a 2-position or a 3-position with respect to the ring nitrogen atom in the 1-position, the 2-position being of particular interest. Likewise, in all compounds of the formula I containing a diaza-arenecarboxamide moiety of the formulae IIIe to IIIIj and containing only one Y group which is a carbon atom bonded to a group of the formula II, the group of the formula II can be present in any position. For example, in a compound of the formula I containing a pyrimidine-4-carboxamide moiety of the formula IIIh, the group of the formula II can be present in the 2-position (formula IIIh-1), or the 5-position (formula IIIh-2), or the 6-position (formula IIIh-3) with respect to the ring nitrogen atoms in positions 1 and 3 and the carboxamide group in position 4, where the 2-position and the 6-position are of particular interest and the 6-position being of special interest. As in the formulae IIIh-1 to IIIh-3, in the pyridinecarboxamide moieties and diaza-arenecarboxamide moieties mentioned above, all ring positions which are not occupied by the group of the formula II or are not nitrogen atoms, carry identical or different $R^1$ groups.

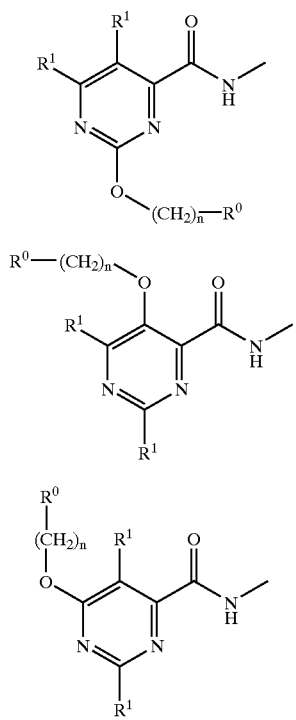

Preferably only one of the Y groups in the aromatic ring system $CY_5$ of formula I is a carbon atom bonded to a group of the formula II, and the other of the Y groups are nitrogen atoms or carbon atoms bonded to a group $R^1$ as outlined above.

The integer n preferably is 1, 2, 3, or 4, particularly 1, 2 or 3, especially 2.

The group $R^0$ present in the groups of the formula II can be, for example, phenyl, pyridinyl including pyridin-2-yl, pyridin-3-yl, and pyridin-4-yl, pyridazinyl including pyridazin-3-yl and pyridazin-4-yl, pyrimidinyl including pyrimidin-2-yl, pyrimidin-4-yl, and pyrimidin-5-yl, or pyrazinyl including pyrazin-2-yl. In one embodiment of the present invention, $R^0$ is phenyl, pyridinyl, or pyrimidinyl, especially phenyl or pyridinyl, very especially phenyl. A pyridinyl group representing $R^0$ of particular interest is pyridin-2-yl or pyridin-4-yl, a pyrimidinyl group representing $R^0$ of particular interest is pyrimidin-4-yl. The $R^0$ groups can be unsubstituted, or substituted by one, two, three, four, or five identical or different substituents. In one embodiment of the present invention, the $R^0$ groups are unsubstituted, or substituted by one, two, or three identical or different substituents. In another embodiment of the present invention, the $R^0$ groups are unsubstituted, or substituted by one or two identical or different substituents. As outlined above with respect to aryl groups and heteroaryl groups in general, substituents in a group $R^0$ can be present in any position. Thus, for example, a monosubstituted phenyl group representing $R^0$ can be 2-substituted, 3-substituted, or 4-substituted. A particularly interesting monosubstituted phenyl group representing $R^0$ is 2-substituted or 4-substituted. A disubstituted phenyl group representing $R^0$ can be 2,3-substituted, 2,4-substituted, 2,5-substituted, 2,6-substituted, 3,4-substituted, or 3,5-substituted by identical or different substituents. A particularly interesting disubstituted phenyl group representing $R^0$ is 2,4-substituted phenyl. Thus, in one embodiment of the present invention, $R^0$ is phenyl which is unsubstituted or substituted by one or two identical or different substituents $R^2$, especially where the substituents are present in positions 2 and/or 4.

The $R^1$ groups are preferably selected from hydrogen, halogen, hydroxy, nitro, $R^{11}R^{12}N$, and $(C_1-C_8)$-alkyloxy, where a $(C_1-C_8)$-alkyloxy group representing $R^1$ of particular interest is $(C_1-C_4)$-alkyloxy, especially methoxy, and where a group $R^{11}R^{12}N$— of particular interest representing $R^1$ is the amino group $NH_2$. If an alkyl group or aryl group present in a group $R^1$ is substituted by one or more identical or different substituents $R^{13}$, in one embodiment it is substituted by one, two, three, four, or five identical or different substituents $R^{13}$. If an alkyl group or aryl group present in a group $R^1$ is substituted by one or more identical or different substituents $R^{13}$, in another embodiment it is substituted by one, two, or three, identical or different substitutents $R^{13}$. Examples of $R^1$ groups in which an alkyl group or aryl group is substituted by $R^{13}$ are aminomethyl, hydroxymethyl, trifluoromethyl, trifluoromethoxy, 2,2,3,3,3-pentafluoropropoxy, 2-methoxyethoxy, or 3,4-dimethoxyphenyl.

The number of the $R^1$ groups which can be present in the aromatic ring system $CY_5$ depends on the number of the groups of the formula II and the number of ring nitrogen atoms that are present, and can be zero, one, two, three, or four. Particular embodiments of the invention are compounds where one, two, or three of the R1 groups that are present have any one of the meanings of $R^1$ given above, including hydrogen, and a fourth group $R^1$ that may be present is hydrogen. Another embodiment of the invention is where one or two of the $R^1$ groups that are present have any one of the meanings of $R^1$ given above, including hydrogen, and a third and fourth group $R^1$ that may be present are hydrogen. For example, in compounds of the formula I which contain a benzamide moiety of the formula IIIa and only one group of the formula II, one, two, or three of the four $R^1$ groups that are present denote hydrogen or a group different from hydrogen, and the fourth group $R^1$ denotes hydrogen. In another embodiment of the present invention, compounds of the formula I contain a benzamide moiety of the formula IIIa and only one group of the formula II, where one or two of the four $R^1$ groups that are present denote hydrogen or a group different from hydrogen, and the third and the fourth $R^1$ group denote hydrogen. Moreover, in the case of compounds of the formula I which contain a benzamide moiety of the formula IIIa and only one group of the formula II, in another embodiment of the present invention one or two $R^1$ groups are different from hydrogen and three or two $R^1$ groups are hydrogen.

In the case of compounds of the formula I which contain a pyridinecarboxamide or a diaza-arenecarboxamide moiety of the formulae IIIb to IIIj and only one group of the formula II, a particular embodiment of the present invention is one in which all $R^1$ groups are hydrogen, or one $R^1$ group is different from hydrogen and the remaining $R^1$ groups are hydrogen.

Any R¹ groups that are different from hydrogen can be present in any desired position of the aromatic ring system $CY_5$, provided a sufficiently stable molecule results that is suitable for the desired purpose. For example, if a compound of the formula I contains a benzamide moiety of the formula IIIa, only one group of the formula II, and one or two R¹ groups that are different from hydrogen, those R¹ groups can be present in any of the positions 2, 3, 4, 5, and 6 (with respect to the amide group C(=O)—NH in the 1-position), as far as the respective positions are not occupied by the group of the formula II. If in the case of a compound of the formula I containing a benzamide moiety of the formula IIIa and a single group of the formula II in the 3-position (with respect to the amide group C(=O)—NH in the 1-position), a single R¹ group that is different from hydrogen is present, in one embodiment of interest the R¹ group is present in the 4-position or in the 5-position, especially in the 4-position. If in the case of a compound of the formula I containing a benzamide moiety of the formula IIIa and a single group of the formula II in the 3-position (with respect to the amide group C(=O)—NH in the 1-position), two groups R¹ that are different from hydrogen are present, in one embodiment of the present invention these groups are present in positions 4 and 5.

Besides the above embodiments, other embodiments of the present invention have the ring system $CY_5$ and substituents R¹ together forming a polycyclic aromatic ring system. If two R¹ groups bonded to adjacent ring carbon atoms together with the carbon atoms to which they are bonded form an aromatic ring fused to the ring $CY_5$ depicted in formula I, the resulting bicyclic aromatic ring system particularly may comprise two fused 6-membered rings. One of the two fused 6-membered rings, i.e., the ring $CY_5$ of the formula I which is bonded to the groups of the formula II, contains zero, one, or two ring nitrogen atoms, and the second ring, i.e., the additional ring formed by the two R¹ groups, may particularly be a benzene ring comprising only carbon ring atoms. Thus, in this latter embodiment of the invention the two residues R¹— which are bonded to adjacent carbon atoms and which together with the carbon atoms to which they are bonded form a condensed benzene ring, can be regarded as forming a divalent residue of the formula —C(R¹⁵)=C(R¹⁵)—C(R¹⁵)=C(R¹⁵)— the terminal carbon atoms of which are bonded to two adjacent carbon atoms in the ring system $CY_5$, and in which the R¹⁵ groups which are identical or different, are independently selected from hydrogen and R¹³. Examples of parent structures from which such a condensed aromatic ring system can be derived are naphthalene, quinoline, isoquinoline, cinnoline, quinazoline, quinoxaline, and phthalazine. The amide group C(=O)—NH— and the groups of the formula II can be located in any position in the ring which corresponds to the ring $CY_5$ of formula I. Thus, the compounds of the formula I can, inter alia, contain a naphthalene-1-carboxamide moiety of the formula IIIk, a naphthalene-2-carboxamide moiety of the formula IIIm, a quinoline-2-carboxamide moiety of the formula IIIn, a quinoline-3-carboxamide moiety of the formula IIIo, a quinoline-4-carboxamide moiety of the formula IIIp, an isoquinoline-1-carboxamide moiety of the formula IIIq, an isoquinoline-3-carboxamide moiety of the formula IIIr, or a quinazoline-2-carboxamide moiety of the formula IIIs:

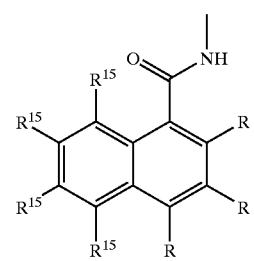

IIIk

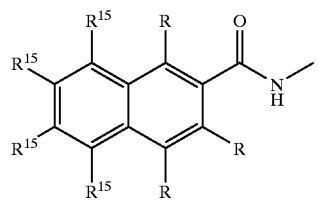

IIIm

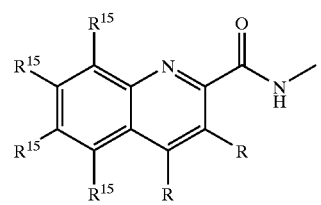

IIIn

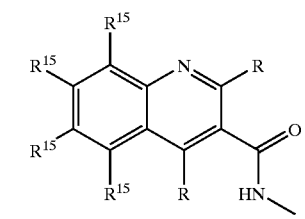

IIIo

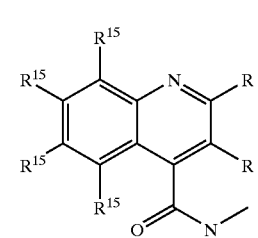

IIIp

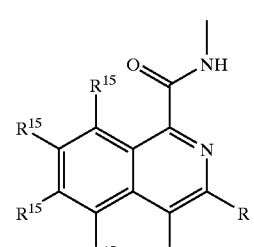

IIIq

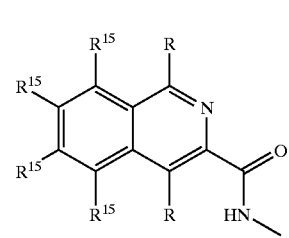

IIIr

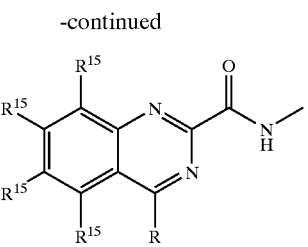

IIIs in all of which one or two of the R groups are identical or different groups of the formula II, and the remaining R groups are identical or different $R^1$ groups, and the $R^{15}$ groups are identical or different groups selected from hydrogen and $R^{13}$. As in the cases were the ring system $CY_5$ is a monocyclic ring, R groups representing groups of the formula II can be present in any position. For example, if a compound of the formula I contains a naphthalene-1-carboxamide moiety of the formula IIIk, and only one group of the formula II is present, it can be present in positions 2, 3, and 4 of the naphthalene system of which the 3-position is of particular interest. If a compound of the formula I contains a naphthalene-2-carboxamide moiety of the formula IIIm and only one group of the formula II is present, it can be present in positions 1, 3, and 4 of the naphthalene system of which the 4-position is of particular interest. If a compound of the formula I contains a quinoline-2-carboxamide moiety of the formula IIIn, and only one group of the formula II is present, it can be present in positions 3 and 4 of the quinoline system, where the 4-position is of particular interest.

In one embodiment of the present invention, the $R^2$ groups which may be present in the $R^0$ group are selected from halogen and $(C_1–C_4)$-alkyl, where alkyl groups representing $R^2$ are unsubstituted, or substituted by one or more identical or different halogen atoms. In another embodiment, the $R^2$ groups are identical or different halogen atoms, wherein in a further embodiment these halogen atoms are selected from fluorine, chlorine, and bromine. If an alkyl group present in a $R^2$ group is substituted by one or more identical or different halogen atoms, in one embodiment of the present invention, it is substituted by one, two, three, four, or five identical or different halogen atoms, and in a further embodiment it is substituted by one, two, or three identical or different halogen atoms. Examples of $R^2$ groups in which an alkyl group is substituted by halogen atoms are trifluoromethyl, trifluoromethoxy or 2,2,3,3,3-pentafluoropropoxy.

If the alkyl, aryl, and Het groups present in $R^3$, $R^4$, and $R^5$ are substituted by one or more identical or different substituents $R^{13}$, in one embodiment of the present invention they are substituted by one, two, three, four, or five identical or different substituents $R^{13}$, and in another embodiment of the present invention they are substituted by one, two, or three identical or different substituents $R^{13}$. The identical or different substituents $R^{13}$ can be present in any position(s), provided that a stable molecule results which is suitable for the desired purpose.

In one embodiment, $R^3$ is hydrogen or $(C_1–C_6)$-alkyl, where the alkyl group representing $R^3$ is unsubstituted, or substituted by one or more identical or different substituents $R^{13}$. In another embodiment, one of the groups $R^4$ and $R^5$ is hydrogen or $(C_1–C_4)$-alkyl, especially hydrogen, and the other of the groups $R^4$ and $R^5$ is selected from hydrogen, $(C_1–C_{12})$-alkyl, $(C_6–C_{14})$-aryl-$(C_1–C_4)$-alkyl-, $(C_6–C_{14})$-aryl-, Het-, and Het-$(C_1–C_4)$-alkyl-, where the groups alkyl, aryl, and Het present in $R^4$ and $R^5$ are unsubstituted, or substituted by one or more identical or different substituents $R^{13}$. In yet another embodiment, $R^4$ and $R^5$ together with the nitrogen atom to which they are bonded form a saturated 3-membered to 8-membered heterocyclic ring which in addition to the nitrogen atom carrying $R^4$ and $R^5$ can contain one or two identical or different ring heteroatoms selected from oxygen, sulfur, and nitrogen. In one embodiment of the present invention, wherein a heterocyclic ring is formed by $R^4$ and $R^5$ together with the nitrogen atom to which they are bonded, that ring contains no additional ring heteroatom, or else contains only one additional ring heteroatom selected from nitrogen, oxygen, and sulfur. Examples of such heterocyclic rings are aziridine, azetidine, pyrrolidine, 1,2-oxazolidine, 1,3-oxazolidine, 1,2-thiazolidine, 1,3-thiazolidine, piperidine, morpholine, thiomorpholine, piperazine, perhydroazepine, or perhydroazocine, all of which are bonded via a ring nitrogen atom and can be substituted as outlined above. Heterocyclic rings formed by $R^4$ and $R^5$ together with the nitrogen atom to which they are bonded, such as aziridine, azetidine, pyrrolidine, and piperidine, are particular embodiments of the present invention.

If alkyl and aryl groups present in $R^{11}$ and $R^{12}$ are substituted by one or more identical or different substituents $R^{13}$, they maybe substituted by one, two, three, four, or five, in particular by one, two, or three, identical or different substituents $R^{13}$, which substituents can be present in any position(s), provided that a stable molecule results which is suitable for the desired purpose. A heterocyclic ring formed by $R^{11}$ and $R^{12}$ together with the nitrogen atom to which they are bonded preferably does not contain a further ring heteroatom, or contains one further ring heteroatom selected from nitrogen, oxygen, and sulfur in addition to the nitrogen atom carrying $R^{11}$ and $R^{12}$. The ring heteroatoms can be present in any desired positions. One embodiment of the present invention has a saturated heterocyclic ring. In another embodiment, where the ring is unsaturated, it may contain one or two double bonds. Heterocyclic rings with 5 or 6 members are an embodiment of the present invention. Examples of such heterocyclic rings are aziridine, azetidine, pyrrolidine, pyrroline, 1,2-oxazolidine, 1,3-oxazolidine, 2,3-dihydro-1,3-oxazole, 1,2-thiazolidine, 1,3-thiazolidine, 2,3-dihydro-1,3-thiazole, piperidine, 1,2-dihydropyridine, 1,4-dihydropyridine, 1,2,3,4-tetrahydropyridine, 1,2,3,6-tetrahydropyridine, morpholine, thiomorpholine, piperazine, perhydroazepine, or perhydroazocine all of which are bonded via a ring nitrogen atom. A heterocyclic ring formed by $R^{11}$ and $R^{12}$ together with the nitrogen atom to which they are bonded can be unsubstituted, or substituted as described above with respect to heterocyclic groups in general. In particular, in a heterocyclic ring formed by $R^{11}$ and $R^{12}$ together with the nitrogen atom to which they are bonded, one or two ring carbon atoms can be substituted by an oxo group, i.e., can be bonded to a doubly bonded oxygen atom, resulting in one or two carbonyl groups >C=O as ring members. Carbon atoms substituted by oxo can be present in any positions, including the positions adjacent to ring heteroatoms, and in particular may be present in the positions adjacent to the nitrogen atom carrying the groups $R^{11}$ and $R^{12}$. Examples of such oxo-substituted heterocyclic ring are pyrrolidine-2,5-dione, imidazolidine-2,4-dione, oxazolidine-2,4-dione, pyrrolidine-2-one, imidazolidin-2-one, pyrazolidine-3,5-dione, piperidine-2-one, piperazine-2-one, morpholine-3-one, piperidine-2,6-dione, etc.

Particular embodiments of the invention are compounds of the formula I in which one or more of the groups or residues or numbers have particular denotations or have one or more specific denotations of the denotations listed in their respective definitions and the general explanations relating to the respective groups and residues. All combinations of such particular denotations and specific denotations are a subject of the present invention. As with the compounds of the formula I in general, the particularly embodied compounds of the formula I are a subject of the present invention in all their stereoisomeric forms and mixtures thereof in any ratio, and in the form of their physiologically tolerable salts. Further embodiments of the present invention encompass compounds of the formula I in the form of their prodrugs and other derivatives as explained above, for example, in the form of their esters or amides, such as unsubstituted amides, $(C_1-C_8)$-alkyl amides, and other amides, or their acyl prodrugs or carbamate prodrugs.

For example, compounds of the formula I of particular interest are compounds in which one of the Y groups is a carbon atom carrying a group of the formula II,

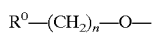  II zero, one, or two of the Y groups are nitrogen atoms, and the remaining Y groups are carbon atoms bonded to a group $R^1$, where the Y groups are selected independently of each other, and can be identical or different;

A is $R^4R^5N—$;

k is 3;

n is 2;

$R^0$ is phenyl which is unsubstituted, or substituted by one or two identical or different substituents;

in all their stereoisomeric forms and mixtures thereof in any ratio, and their physiologically tolerable salts.

The present invention also relates to processes of preparation by which the compounds of the formula I are obtainable. The compounds of the formula I can generally be prepared by linking of two or more fragments (or building blocks) which can be derived retrosynthetically from the formula I. In preparation of the compounds of the formula I, it can generally be advantageous or necessary in the course of the synthesis to introduce functional groups which could lead to undesired reactions or side reactions in a synthesis step in the form of precursors which are later converted into the desired functional groups, or to temporarily block functional groups by a protective group strategy suited to the synthetic problem. Such strategies are well known to those skilled in the art (see, for example, Greene and Wuts, *Protective Groups in Organic Synthesis*, John Wiley & Sons, 1991). Nitro groups are examples of precursor groups which can later be converted by reduction, for example, by catalytic hydrogenation, into amino groups. Protecting groups (or blocking groups) that may be present on functional groups include allyl, tert-butyl, benzyl, tert-butyloxycarbonyl (Boc), benzyloxycarbonyl (Z), and 9-fluorenylmethyloxycarbonyl (Fmoc) as protecting groups for hydroxy, carboxylic acid, amino, and guanidino groups.

In particular, in preparation of the compounds of the formula I, building blocks can be connected by performing one or more condensation reaction such as amide couplings or ester formations, i.e., by forming amide bonds or ester bonds between a carboxylic acid group of one building block and an amino group or hydroxy group of another building block, or by establishing an ether linkage between a hydroxy group or a halogen atom of one building block and an hydroxy group of another building block. For example, compounds of the formula I can be prepared by linking the building blocks of the formulae IV, V, VI, and VII

 IV

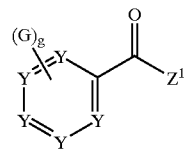 V

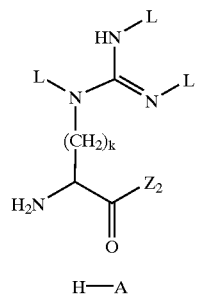 VI

H—A  VII by means of forming, in a manner known in the art, an amide bond between the carboxylic acid derivative group CO—$Z^1$ of formula V and the $NH_2$ group depicted in formula VI, by forming in a manner known in the art one or two ether linkages between building blocks of the formulae IV and V in which groups E and/or groups G are hydroxy groups, and by optionally forming in a manner known in the art an amide bond or an ester bond between the carboxylic acid derivative group CO—$Z^2$ and the amino or oxy group to which the hydrogen atom of formula VII is bonded.

In the compounds of formulae IV, V, VI, and VII the groups A, L, and $R^0$ and n and k are defined as above, but functional groups in these compounds can also be present in the form of precursor groups which are later converted into the groups present in the compounds of the formula I, or functional groups can be present in protected form. One or two of the Y groups in the compounds of the formula V are carbon atoms to which the G groups are bonded, zero, one, two, or three of the Y groups are nitrogen atoms, and the remaining Y groups are carbon atoms bonded to a group $R^1$, where $R^1$ is defined as above but where functional groups in $R^1$ can also be present in the form of precursor groups which are later converted into the groups present in the compounds of the formula I, or functional groups can be present in protected form. If compounds of the formula I are to be prepared in which one group of the formula II is present, the integer g of the groups G that are present in the compounds of the formula V is one. If compounds of the formula I are to be prepared in which two groups of the formula II are present, the integer g is two. The groups G which can be identical or different, are hydroxy groups or nucleophilically substitutable leaving groups, for example, halogen like fluorine, chlorine, bromine, or iodine. Similarly, the group E in the compounds of the formula IV is a hydroxy group or a nucleophilically substitutable leaving group, for example, halogen such as chlorine, bromine, or iodine, or a sulfonyloxy group such as tosyloxy, methylsulfonyloxy, or trifluoromethylsulfonyloxy. At least one of the two groups E and G which are reacted to establish an ether linkage via which the group $R^0$—$(CH_2)_n$ is attached, must be a hydroxy group. The groups $Z^1$ and $Z^2$, which can be identical or different, are hydroxy or nucleophilically substitutable leaving groups, i.e., the groups $COZ^1$ and $COZ^2$ in the compounds of the formulae V and VI are carboxylic acid groups COOH, or activated derivatives of carboxylic acids, such as acid chlorides, esters such as $(C_1-C_4)$-alkyl esters or activated esters, or mixed anhydrides.

The starting compounds of the formulae IV, V, VI, and VII, and other compounds which are employed in the synthesis of the compounds of formula I for introducing certain structural units, are commercially available or can be readily prepared from commercially available compounds by, or analogously to, procedures described below or in the literature readily available to those skilled in the art.

For the preparation of the compounds of formula I, first the compounds of the formulae IV and V may be linked and the resulting intermediate product then be condensed with a compound of the formula VI to give an intermediate product which is finally condensed with a compound of the formula VII to give a compound of the formula I. Similarly, first the compounds of the formulae VI and VII may be condensed and the resulting intermediate product then be condensed with a compound of the formula V to give an intermediate product which is finally linked to a compound of the formula IV to give a compound of the formula I. The intermediate obtained from the compounds of the formula VI and VII may also be condensed with an intermediate obtained by condensing the compounds of the formulae IV and V. There are various other possibilities how the compounds of the formulae IV, V, VI, and VII can be coupled to give compounds of the formula I. After any such reaction step in the course of such syntheses, protecting and deprotecting steps and conversions of precursor groups into the desired final groups may be carried out and further modifications may made. For example, a group like $R^1$ that is different from hydrogen may already be present in the compound of formula V which is employed into the coupling reaction with the compound of formula VI or with the intermediate obtained from the compounds of formula VI and VII, but such a group $R^1$ may also be introduced only after performing one coupling reaction or both coupling reactions. The synthetic strategy for the preparation of a compound of the formula I can thus be broadly varied, and the individual case determines which synthetic procedure is preferred.

Various general methods for the formation of an amide bond that can be employed in the synthesis of the compounds of formula I are known to those skilled in the art, for example, from peptide chemistry. An amide coupling or ester coupling step can favorably be carried out by employing a free carboxylic acid, i.e., a compound of the formula V or VI or an intermediate coupling product in which a group like $COZ^1$ or $COZ^2$ reacting in that step is a COOH group, activating that carboxylic acid group, preferably in situ, by means of a customary coupling reagent, such as a carbodiimide like dicyclohexylcarbodiimide (DCC) or diisopropylcarbodiimide (DIC), or a carbonyldiazole like carbonyldiimidazole, or a uronium salt like O-((cyano-(ethoxycarbonyl)methylene)amino)-1,1,3,3-tetramethyluronium tetrafluoroborate (TOTU) or O-(7-azabenzotriazol-1-yl)-1,1,3,3-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound or hydroxy compound of the formula VI or VII. An amide bond can also be formed by reacting an amino compound with a carboxylic acid halide, in particular with a carboxylic acid chloride, which can be prepared in a separate step or in situ from a carboxylic acid and, for example, thionyl chloride, or an carboxylic acid ester or thioester, for example, a methyl ester, ethyl ester, phenyl ester, nitrophenyl ester, pentafluorophenyl ester, methylthio ester, phenylthio ester, or pyridin-2-ylthio ester, i.e., with a compound of the formula V or VI or with a intermediate coupling product in which a group like $Z^1$ or $Z^2$ is chlorine, methoxy, ethoxy, optionally substituted phenyloxy, methylthio, phenylthio, or pyridin-2-ylthio.

The activation reactions and coupling reactions are usually performed in the presence of an inert solvent (or diluent), for example, in the presence of an aprotic solvent like dimethylformamide (DMF), tetrahydrofuran (THF), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and may be, for example, from about $-20°$ C. to the boiling temperature of the solvent or diluent. Also depending on the specific process, it may be necessary or advantageous to add in a suitable amount one or more auxiliary agents, for example, a base like a tertiary amine, such as triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references, such as J. March, *Advanced Organic Chemistry*, 4th ed., John Wiley & Sons, 1992; or Houben-Weyl, *Methoden der organischen Chemie* (*Methods of Organic Chemistry*), Georg Thieme Verlag.

The formation of the ether linkage between the building blocks of the formulae IV and V by condensation of the groups E and G can be performed by various methods which are known per se and which are familiar to those skilled in the art. If in a compound of the formula IV wherein n is not zero, the group E is halogen, sulfonyloxy, or another nucleophilically substitutable leaving group, and the group G is hydroxy, the reaction is between a substituted alkyl halide, etc., and an aromatic, i.e., phenolic, or a heteroaromatic hydroxy group, and corresponds to the well known Williamson reaction. If E is hydroxy and G is halogen or another nucleophilically substitutable leaving group, the reaction is between an alcohol or phenol and an aryl or heteroaryl halide, etc., and is an aromatic nucleophilic substitution. The latter reaction can be carried in case the aromatic ring in the compound of the formula V is activated by electron-withdrawing substituents like nitro or by ring nitrogen atoms. Details for performing these standard reactions, for example, with regard to solvents or to the addition of bases, can be found in the above-mentioned references such as J. March, Houben-Weyl, and references cited therein. A versatile method which can favorably be used to form the ether linkage is the condensation of compounds of the formulae IV and V wherein both E and G are hydroxy, under Mitsunobu reaction conditions. In such a reaction, a hydroxy compound is activated by reaction with an azodicarboxylic acid ester, such as diethyl azodicarboxylate (DEAD) or diisopropyl azodicarboxylate (DIAD), and a phosphane, such as triphenylphosphane or tributylphosphane, and becomes susceptible to nucleophilic substitution by, for example, a second hydroxy compound. The reaction can usually be carried under mild conditions in an aprotic solvent, such as an ether, for example, tetrahydrofuran or dioxane, at temperatures from about 0° C. to about room temperature. Details on the Mitsunobu reaction are given, for example, in O. Mitsunobu, *Synthesis* (1981) 1–28, or in the examples below.

Protective groups that may still be present in the products obtained in the above reactions are then removed by standard procedures. For example, tert-butyl protecting groups, in particular, a tert-butyl ester group which is a protected form of a COOH group, can be deprotected, i.e., converted into the carboxylic acid group in the case of an tert-butyl ester, by treatment with trifluoroacetic acid. Benzyl groups can be removed by hydrogenation. Fluorenylmethoxycarbonyl groups can be removed by secondary amines such as piperidine. As already explained, also after the coupling reaction functional groups can be generated from suitable precursor groups or, if desired, further reactions can be carried out on the coupling products by standard processes, such as acylation reactions or esterification reactions. In addition, a conversion into a physiologically tolerable salt or a prodrug of a compound of the formula I can then be carried out by known processes.

The reactions described above and below that are carried out in the syntheses of the compounds of the formula I can generally be carried out according to the methods of conventional solution phase chemistry, as well as according to the methods of solid phase chemistry which are well known, for example, from peptide synthesis. The compounds of the formula I can be prepared, for example, according to the methods of solid phase chemistry by a process which comprises:

a) coupling a compound of the formula VI, wherein $Z^2$ is hydroxy, the amino group is protected by a Fmoc group, and the L-substituted guanidino group is a protected guanidino group, to an acid sensitive linker attached to a resin, or in general to a solid support, and cleaving off the protecting group Fmoc to generate a free amino group;

b) coupling a compound of the formula V, wherein $Z^1$ is hydroxy, to the free amino group;

c) coupling a compound of the formula IV to the intermediate attached to the resin by reacting the groups E and G to give an ether linkage, for example, coupling a compound of the formula IV in which E is hydroxy to the intermediate in which G is hydroxy under Mitsunobu conditions in the presence of an azodicarboxylate and triphenylphosphane; and d) cleaving off the compound obtained according to steps a) through c) from the resin by means of trifluoroacetic acid.

The resin or the linker used in this process may be of a type such that the carboxy group in the compound of the formula VI which is coupled to the resin or the linker, respectively, is transformed into an amide group C(=O)—$NH_2$, for example, a Knorr Linker or a Rink amide resin.

In general, a reaction mixture containing a final compound of the formula I or an intermediate thereof is worked up and, if desired, the product is then purified by customary processes known to those skilled in the art. For example, a synthesized compound can be purified using well known methods such as crystallization, chromatography, or reverse phase high performance liquid chromatography (RP-HPLC), or other methods of separation based, for example, on the size, charge, or hydrophobicity of the desired compound or compounds. Similarly, well known methods such as NMR, IR, and mass spectrometry (MS) can be used for characterizing a compound of the invention.

The compounds of the present invention are serine protease inhibitors which inhibit the activity of at least one of the blood coagulation enzymes factor Xa and factor VIIIa. In one embodiment, they are highly active inhibitors of factor Xa. Compounds of the invention are specific serine protease inhibitors in so far as they do not substantially inhibit the activity of other proteases involved in the blood coagulation and/or the fibrinolysis pathway whose inhibition is not desired, such as plasmin and thrombin. In an embodiment of the invention, the inventive compounds do not substantially inhibit thrombin at concentrations which inhibit at least one of factor Xa and factor VIIa.

The activity of the compounds of the formula I can be determined, for example, in the assays described below, or in other assays known to those skilled in the art. With respect to factor Xa inhibition, one embodiment of the invention comprises compounds wherein $K_i \leq 1$ $\mu$M for factor Xa inhibition as determined in the assay described below, with or without concomitant factor VIIa inhibition, and which optionally do not substantially inhibit the activity of other proteases involved in coagulation and fibrinolysis whose inhibition is not desired (using the same concentration of the inhibitor). Another embodiment comprises compounds where the factor Xa inhibition has a $K_i$ which is $\leq 0.1$ $\mu$M. The compounds of the invention inhibit factor Xa catalytic activity either directly, within the prothrombinase complex or as a soluble subunit, or indirectly, by inhibiting the assembly of factor Xa into the prothrombinase complex.

With respect to factor VIIa inhibition, one embodiment of the invention comprises compounds which have a $K_i \leq 10$ $\mu$M for factor VIIa inhibition as determined in the assay described below, with or without concomitant factor Xa inhibition. In another embodiment of the invention, these compounds which have a $K_i \leq 10$ $\mu$M for factor VIIa inhibition do not substantially inhibit the activity of other proteases involved in coagulation and fibrinolysis whose inhibition is not desired (using the same concentration of the inhibitor).

Because of their factor Xa and/or factor VIIa inhibitory activity the compounds of the formula I are useful pharmacologically active compounds which are suitable, for example, for influencing blood coagulation (or blood clotting) and fibrinolysis, and for the therapy and prophylaxis of, for example, cardiovascular disorders, thromboembolic diseases, or restenoses. The compounds of the formula I and their physiologically tolerable salts and their prodrugs can be administered to animals, particularly to mammals, and especially to humans as pharmaceuticals for therapy or prophylaxis. They can be administered on their own, or in mixtures with one another or in the form of pharmaceutical preparations which permit enteral or parenteral administration and which contain, as active constituent, an effective amount of at least one compound of the formula I and/or its physiologically tolerable salts and/or its prodrugs in addition to customary pharmaceutically acceptable carrier substances and/or additives.

The present invention therefore also relates to the compounds of the formula I and/or their physiologically tolerable salts and/or their prodrugs for use as pharmaceuticals (or medicaments). The invention further relates to uses of the compounds of the formula I and/or their physiologically tolerable salts and/or their prodrugs for the production of pharmaceuticals for the inhibition of factor Xa and/or factor VIIa or for influencing blood coagulation or fibrinolysis or for the therapy or prophylaxis of the diseases mentioned herein, for example, for the production of pharmaceuticals for the therapy and prophylaxis of cardiovascular disorders, thromboembolic diseases, or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned herein, for example, for use in the therapy and prophylaxis of cardiovascular disorders, thromboembolic diseases, or restenoses, and to methods of treatment aiming at such purposes including methods for said therapies and prophylaxes. The present invention furthermore relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e., one or more pharmaceutically acceptable carrier substances or excipients and/or auxiliary substances or additives.

The pharmaceutical preparations and compositions can be administered orally, for example, in the form of pills, tablets, lacquered tablets, coated tablets, granules, hard and soft gelatin capsules, solutions, syrups, emulsions, suspensions, or aerosol mixtures. Administration can also be carried out rectally, for example, in the form of suppositories, or parenterally, for example, intravenously, intramuscularly, or subcutaneously, in the form of injection solutions or infusion solutions, microcapsules, implants, or rods, or percutaneously or topically, for example, in the form of ointments, solutions, or tinctures, or in other ways known to those of skill in the relevant art, for example, in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatin capsules it is possible to use, for example, lactose, corn starch, or derivatives thereof, talc, stearic acid, or its salts, etc. Carrier substances for soft gelatin capsules and suppositories are, for example, fats, waxes, semisolid and liquid polyols, natural or hardened oils, etc. Suitable carrier substances for the production of solutions, for example, injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 to about 1000 mg, particularly from about 1 to about 500 mg.

In addition to the active ingredients of the formula I and/or their physiologically acceptable salts and/or prodrugs and to carrier substances, the pharmaceutical preparations and compositions can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents, and/or antioxidants. They can also contain two or more compounds of the formula I and/or their physiologically tolerable salts and/or their prodrugs. In cases where a pharmaceutical preparation or composition contains two or more compounds of the formula I, the selection of the individual compounds can aim at producing a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds, and thus allows the selection of such desired compounds. Furthermore, in addition to at least one compound of the formula I and/or its physiologically tolerable salts and/or its prodrugs, the pharmaceutical preparations optionally can also contain one or more other therapeutically or prophylactically active ingredients.

As inhibitors of factor Xa and/or factor VII, the compounds of the formula I and their physiologically tolerable salts and their prodrugs are generally suitable for the therapy and prophylaxis of conditions in which the activity of factor Xa and/or factor VIIa plays a role or has an undesired activity, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired activity, or which can favorably be influenced by reducing blood clotting, or for the prevention, alleviation or cure of which a decreased activity of the blood coagulation system is desired by the physician. A specific subject of the present invention thus is the reduction or inhibition of unwanted blood clotting, in particular in an individual, by administering an effective amount of a compound I or a physiologically tolerable salt or a prodrug thereof, as well as pharmaceutical preparations therefor.

Conditions in which a compound of the formula I can be favorably used include, for example, cardiovascular disorders, thromboembolic diseases or complications associated, for example, with infection or surgery. The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis (for example, restenosis following angioplasty like PTCA), adult respiratory distress syndrome, multi-organ failure, stroke, and disseminated intravascular clotting disorder. Examples of related complications associated with surgery are thromboses like deep vein and proximal vein thrombosis which can occur following surgery. In view of their pharmacological activity, the compounds of the invention can replace or supplement other anticoagulant agents such as heparin. The use of a compound of the invention can result, for example, in cost savings as compared to other anticoagulants.

When using the compounds of the formula I, the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is desired. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg (in each case in mg per kg of body weight). The daily dose can be divided, in particular in the case of the administration of relatively large amounts, into several part administrations, such as 2, 3, or 4 part administration. As usual, depending on individual behavior it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I and its salts can be used for diagnostic purposes, for example, in in vitro diagnoses, and as an auxiliary in biochemical investigations. For example, a compound of the formula I can be used in an assay to identify the presence of factor Xa and/or factor VIIa or to isolate factor Xa and/or factor VIIa in a substantially purified form. A compound of the invention can be labeled with, for example, a radioisotope, and the complex of labeled compound bound to factor Xa and/or factor VIIa is then detected using a routine method useful for detecting the particular label. Thus, a compound of the formula I or a salt thereof can be used advantageously as a probe to detect the location or amount of factor Xa and/or factor VIIa activity in vivo, in vitro, or ex vivo.

Furthermore, the compounds of the formula I can be used as synthetic intermediates for the preparation of other compounds, in particular of other pharmaceutical active ingredients, which are obtainable from the compounds of the formula I, for example, by introduction of substituents or modification of functional groups.

It is understood that modifications that do not substantially affect the activity of the various embodiments of this invention are included within the invention disclosed herein. Accordingly, the following examples are intended to illustrate but not limit the present invention.

EXAMPLES

Abbreviations Used

| Arginine | Arg |
| tert-Butyl | tBu |
| Dichloromethane | DCM |
| Diethyl azodicarboxylate | DEAD |
| Diisopropyl azodicarboxylate | DIAD |
| N,N'-Diisopropylcarbodiimide | DIC |
| N,N-Diisopropyl-N-ethylamine | DIEA |
| N,N-Dimethylformamide | DMF |
| Dimethylsulfoxide | DMSO |
| N-Ethylmorpholine | NEM |
| 9-Fluorenylmethyloxycarbonyl | Fmoc |
| N-Hydroxybenzotriazole | HOBt |
| Methanol | MeOH |
| 2,2,4,6,7-Pentamethyldihydro benzofuran-5-sulfonyl | PBF |
| Tetrahydrofuran | THF |
| Trifluoroacetic acid | TFA |
| O-((Cyan(ethoxycarbonyl)methylene)amino) 1,1,3,3-tetramethyluronium tetrafluoroborate | TOTU |

When in the final step of the synthesis of a compound an acid such as trifluoroacetic acid or acetic acid was used, for example, when trifluoroacetic acid was employed to remove a tert-butyl group or when a compound was purified by chromatography using an eluent which contained such an acid, in some cases, depending on the work-up procedure (for example, the details of a freeze-drying process), the compound was obtained partially or completely in the form of a salt of the acid used, such as in the form of the acetic acid salt or trifluoroacetic acid salt or hydrochloric acid salt.

Example 1

(S)-4-Nitro-N-(1-carbamoyl-4-guanidinobutyl)-3-[2-(2,4-dichlorophenyl)ethoxy]benzamide

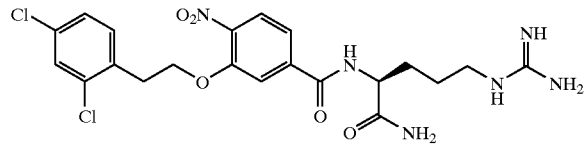

In a reaction vial 300 mg of TENTAGEL® resin functionalized with Rink linker (loading 0.28 mmol/g) was coupled with 600 mg of Fmoc-Arg(Boc)$_2$ in the presence of 151 mg of HOBt and 172 mg of DIC in 3 ml of dry DMF. Coupling was continued overnight at room temperature and was repeated for additional 2 h. The functionalized resin was Fmoc-deprotected by reaction with 50% piperidine in DMF for 15 min. The unprotected resin was washed and coupled with 183 mg of 3-hydroxy-4-nitrobenzoic acid in the presence of 152 mg of HOBt and 176 mg of DIC in 3 ml of dry DMF for 3 h at room temperature. The resin was washed with DMF, MeOH and DCM and dried in vacuo for 3 h. The dried resin was washed with anhydrous THF and mixed with 267 mg of triphenylphosphane and 201 mg of 2-(2,4-dichlorophenyl)ethanol in 2 ml of anhydrous THF. The suspended resin was cooled in a refrigerator for 20 min and mixed with 180 µl of DEAD dissolved in 1 ml of THF. The mixture was coupled for 15 h at room temperature. The resin was washed with THF, DMF, MeOH, and DCM and cleaved with TFA/water (95/5) for 2 h at room temperature. The solution of the final product was filtered off and the filtrate was evaporated to dryness. The residual product was lyophilized from a mixture of acetonitrile and water. The lyophilized solid was purified by HPLC and the final product characterized by electro-spray mass (ES-MS) spectrometry.

MS: 511 (M+H)$^+$

Example 2

(S)-4-Amino-N-(1-carbamoyl-4-guanidinobutyl)-3-[2-(2,4-dichlorophenyl)ethoxy]benzamide

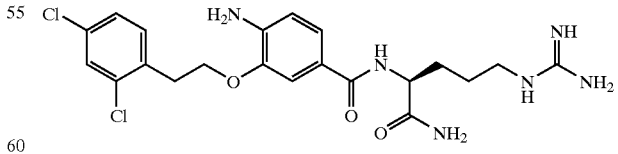

This compound was prepared by a procedure similar to that outlined in Example 1. Before cleaving the final compound from the resin, the resin was mixed with 210 mg of tin chloride and 300 µl of acetic acid in 2.5 ml of DMF. The suspended resin was agitated at room temperature for 8 h.

The resin was washed, dried, and split into three parts. One part was cleaved and processed as outlined in Example 1 to give the title compound. The second and third part were used in Examples 3 and 4.

MS: 481 (M+H)$^+$

Example 3

(S)-4-Acetylamino-N-(1-carbamoyl-4-guanidinobutyl)-3-[2-(2,4-dichlorophenyl)ethoxy]benzamide

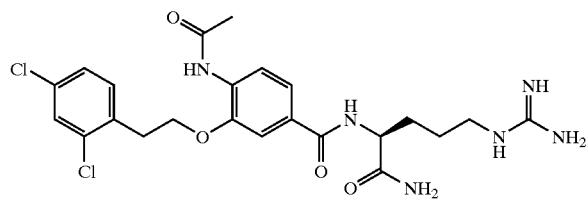

The second part of the resin obtained in Example 2 (105 mg) was washed with DCM containing 10% DIEA and coupled with a mixture of DCM and acetic anhydride (1/1) at room temperature for 15 h. The resin was washed and dried, and the final product was cleaved off and processed as described in Example 1.

MS: 523 (M+H)$^+$

Example 4

(S)-N-{4-(1-Carbamoyl-4-guanidinobutylcarbamoyl)-2-[2-(2,4-dichlorophenyl)ethoxy]phenyl}succinamic acid

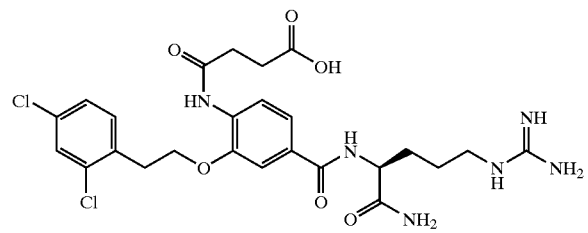

The third part of the resin obtained in Example 2 (116 mg) was coupled with 160 mg of succinic anhydride analogously to the procedure described in Example 3. The resin was washed and dried, and the final product was cleaved off and processed as described in Example 1.

MS: 580.9 (M+H)$^+$

Example 5

(S)-4-Bromo-N-(1-carbamoyl-4-guanidinobutyl)-3-[2-(2,4-dichlorophenyl)-ethoxy]-5-hydroxybenzamide Rink resin (500 mg; loading 0.3 mmol/g) functionalized with Arg(Boc)$_2$ was coupled with 176 mg of 3,5-dihydroxy-4-bromobenzoic acid in the presence of DIC (110 mg) and HOBt (78 mg) in DMF. The resin was then washed and treated with a 30% solution of benzyltrimethylammonium hydroxide in DMF for 1 h. The resin was washed with DMF, 10% acetic acid in DMF, DMF, and DCM and dried in vacuo for 3 h. The dried resin was washed with anhydrous THF and mixed with 0.2 mmol of triphenylphosphane and 0.2 mmol of 2-(2,4-dichlorophenyl)ethanol in 2 ml of dry THF. The suspension of the resin was cooled in a refrigerator for 16 min and 50 µl (0.2 mmol) of DIAD in 0.5 ml of dry THF were added. Coupling was continued overnight at room temperature. The resin was washed with dry THF and the coupling was repeated for additional 8 h. The resin was washed and dried, and the final product was cleaved off and processed as described in Example 1.

MS: 561.8 (M+H)$^+$

Example 6

(S)-N-(1-Carbamoyl-4-guanidinobutyl)-3-[2-(2,4-dichlorophenyl)ethoxy]-5-hydroxy4-methylbenzamide Rink resin (239 mg; loading 0.43 mmol/g) functionalized with Arg(Boc)$_2$ was coupled with 106 mg of 3,5-dihydroxy-4-methylbenzoic acid in the presence of DIC (85 mg) and HOBt (90 mg) in DMF (1.5 ml). The resin was then washed and treated with a 15% solution of benzyltrimethylammonium hydroxide in DMF for 45 min. The resin was washed with DMF, 10% acetic acid in DMF, DMF and DCM and dried in vacuo for 4 h. The dried resin was washed with anhydrous THF and mixed with 145 mg (0.5 mmole) of triphenylphosphane and 25 µl of bistrimethylsilylacetamide in THF and kept at room temperature for 1 h. In a separate vial a mixture of 100 mg (0.2 mmol) of 2-(2,4-dichlorophenyl)ethanol and 100 µl of DIAD in dry THF was prepared. The reaction mixture was added to the resin which had previously been cooled in a refrigerator for 10 min. Coupling was continued at room temperature overnight. The resin was washed and dried, and the final product was cleaved off and processed as described in Example 1.

MS: 496.1 (M+H)$^+$

Example 7

(S)-2-Amino-N-(1-carbamoyl-4-guanidino-butyl)-5-[2-(2,4-dichlorophenyl)ethoxy]benzamide

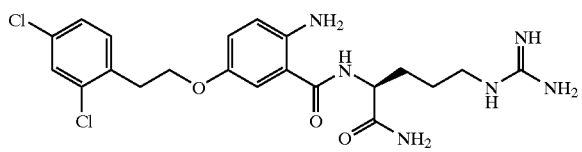

Rink resin (306 mg; loading 0.43 mmol/g) functionalized with Arg(Boc)$_2$ was coupled with 146 mg of 5-hydroxy-2-nitrobenzoic acid in the presence of DIC (136 mg) and HOBt (140 mg) in DMF (2 ml) for 3 h at room temperature. The resin was then washed and treated with a 15% solution of benzyltrimethylammonium hydroxide in DMF for 60 min. The resin was washed with DMF, 10% acetic acid in DMF, DMF and DCM and dried in vacuo for 4 h. The dried resin was washed with anhydrous THF and mixed with 534 mg (2 mmol) of triphenylphosphane, 422 mg (2 mmol) of 2-(2,4-dichlorophenyl)ethanol and 400 µl (2 mmol) of DIAD in dry THF. The mixture was kept overnight at room temperature. The resin was washed and treated with 415 mg of tin dichloride monohydrate in 2 ml of DMF and 0.5 ml of trifluoroethanol. The reduction was continued overnight at room temperature. The resin was washed and dried, and the final product was cleaved off and processed as described in Example 1.

MS: 481 (M+H)$^+$

The following example compounds were prepared analogously to the above examples.

Example compounds of the formula Ia:

| | R$^a$ | MS (M + H)$^+$ |
|---|---|---|
| Example 8 | H | 432.2 |
| Example 9 | CH$_3$ | 446 |
| Example 10 | CH$_3$O | 462.3 |
| Example 11 | NO$_2$ | 477 |

Example compounds of the formula Ib:

| | R$^b$ | MS (M + H)$^+$ |
|---|---|---|
| Example 12 | H | 399.2 |
| Example 13 | CH$_3$ | 413.2 |
| Example 14 | CH$_3$O | 429.2 |
| Example 15 | NO$_2$ | 444.3 |

Example compounds of the formula Ic:

| | R$^c$ | MS (M + H)$^+$ |
|---|---|---|
| Example 16 | H | 412.2 |
| Example 17 | CH$_3$ | 426.2 |
| Example 18 | CH$_3$O | 442.3 |
| Example 19 | NO$_2$ | 457.3 |
| Example 20 | NH$_2$ | 427.2 |

Example compounds of the formula Id:

| | R$^d$ | MS (M + H)$^+$ |
|---|---|---|
| Example 21 | H | 443.3 |
| Example 22 | CH$_3$ | 457.3 |
| Example 23 | CH$_3$O | 473.3 |
| Example 24 | NO$_2$ | 488.3 |
| Example 25 | NH$_2$ | 458.3 |

Example compounds of the formula Ie:

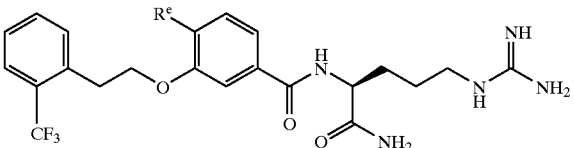

| | $R^e$ | MS (M + H)$^+$ |
|---|---|---|
| Example 26 | H | 466.3 |
| Example 27 | CH$_3$ | 480.3 |
| Example 28 | CH$_3$O | 496.3 |
| Example 29 | NO$_2$ | 511.3 |
| Example 30 | NH$_2$ | 481.3 |

Example compounds of the formula If:

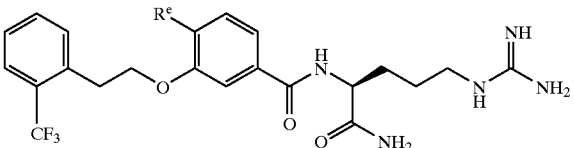

| | $R^f$ | MS (M + H)$^+$ |
|---|---|---|
| Example 31 | 4-nitrophenyl | 494.3 |
| Example 32 | 2,4,6-trimethylphenyl | 491.3 |
| Example 33 | 4-cyanophenyl | 474.3 |
| Example 34 | 2,4-dichlorophenyl | 517.3 |

Example compounds of the formula Ig:

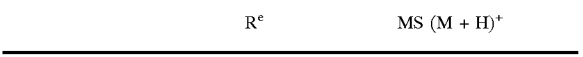

| | $R^g$ | MS (M + H)$^+$ |
|---|---|---|
| Example 35 | 2,4-dichlorophenyl | 468.3 |
| Example 36 | 2,4-dimethoxyphenyl | 474.3 |
| Example 37 | 2,4,6-trimethylphenyl | 442.3 |

Example 38

(S)-3-[2-(2,4-Dichlorophenyl)ethoxy]-N-{4-guanidino-1-[(2-phenylethyl)carbamoyl]butyl}-4-methoxybenzamide

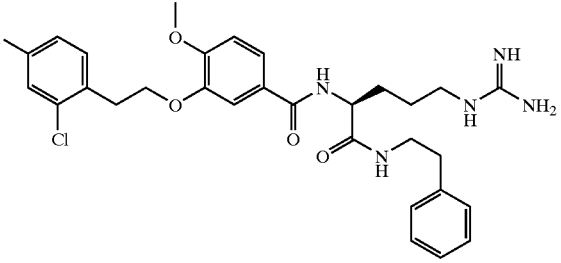

a) 3-[2-(2,4-Dichlorophenyl)ethoxy]-4-methoxybenzoic acid ethyl ester

To a solution of 10 g (38.3 mmol) of triphenylphosphane in 100 ml of THF were added 6.7 g (3.83 mmol) of DEAD over 5 min at room temperature. After 30 min at room temperature, 5 g (25.5 mmol) of 3-hydroxy-4-methoxybenzoic acid ethyl ester and 4.87 g (25.5 mmol) of 2-(2,4-dichlorophenyl)ethanol were added and the mixture was stirred at room temperature for 12 h. The solvent was removed and the residue was separated by chromatography to give 3.6 g (38%) of the title compound.

b) 3-[2-(2,4-Dichlorophenyl)ethoxy]-4-methoxybenzoic acid

A solution of 3.6 g (9.8 mmol) of 3-[2-(2,4-dichlorophenyl)ethoxy]-4-methoxybenzoic acid ethyl ester in 30 ml of ethanol and 5.4 ml of 2N sodium hydroxide solution was stirred at room temperature for 12 h. The precipitate was filtered off. The resulting solid was stirred with 5 ml of 2N HCl and filtered to give 2.44 g (73%) of the title compound.

c) (S)-3-[2-(2,4-Dichlorophenyl)ethoxy]-N-{4-guanidino-1-[(2-phenylethyl)carbamoyl]butyl}-4-methoxybenzamide A solution of 78 mg (0.23 mmol) of Arg-(2-phenylethyl)amide, 100 mg (0.23 mmol) of 3-[2-(2,4-dichlorophenyl)ethoxy]-4-methoxybenzoic acid, 99 mg (0.3 mmol) of TOTU and 78 mg (0.6 mmol) of DIEA in 1.5 ml of DMF was stirred at room temperature for 2 h. 10 ml of DCM was added to the solution, which was then washed with water and dried with sodium sulfate. The solvent was removed and the residue was precipitated with diethyl ether and methanol to give 32 mg (22%) of the title compound.

MS: 600.3 (M+H)$^+$

Example 39

(S)-4-Bromo-3-[2-(2,4-dichlorophenyl)ethoxy]-N-{4-guanidino-1-[(pyridin-3-ylmethyl)carbamoyl]butyl}-5-hydroxybenzamide

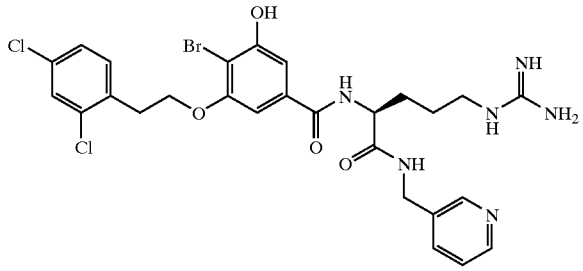

a) 4-Bromo-3-[2-(2,4-dichlorophenyl)ethoxy]-5-hydroxybenzoic acid ethyl ester To a solution of 17.8 g (67.9 mmol) of triphenylphosphane, 8.8 ml (67.9 mmol) of 2-(2,4-dichlorophenyl)ethanol and 16 g (61.3 mmol) of 4-bromo-3,5-dihydroxybenzoic acid ethyl ester in 25 ml of THF was added a solution of 10.6 ml (67.9 mmol) of DEAD in 40 ml of THF within 45 min between 620 and 18° C. After 16 h at room temperature the solvent was removed and the residue was stirred with cyclohexane/ethyl acetate (1/1) and filtered. The solid residue was stirred with cyclohexane and filtered. The remaining solid was separated by chromatography (cyclohexane/ethyl acetate (1/1)) to give 25.6 g (96%) of the title compound.

MS: 433.1 (M+H)$^+$ b) 4-Bromo-3-[2-(2,4-dichlorophenyl)ethoxy]-5-hydroxybenzoic acid

A solution of 25.6 g (59 mmol) of 4-bromo-3-[2-(2,4-dichlorophenyl)ethoxy]-5-hydroxybenzoic acid ethyl ester in 300 ml of ethanol and 2.36 g (65 mmol) of sodium hydroxide in 15 ml of water was stirred at room temperature for 12 h. The solvent was removed and the residue was distributed between water and ethyl acetate. The aqueous solution was acidified with 1 N HCl and the precipitate was filtered to give 4.35 g (31%) of the title compound.

MS: 407.2 (M+H)$^+$ c) (S)-4-Bromo-3-[2-(2,4-dichlorophenyl)ethoxy]-N-{4-guanidino-1-[(pyridin-3-ylmethyl)-carbamoyl]butyl}-5-hydroxybenzamide 25 mg (0.11 mmol) of dicyclohexylcarbodiimide were added to a solution of 40 mg (0.1 mmol) of 4-bromo-3-[2-(2,4-dichlorophenyl)ethoxy]-5-hydroxybenzoic acid, 74 mg (0.1 mmol) of Arg(PBF)-(pyridin-3-ylmethyl)amide, 14 mg (0.1 mmol) of HOBt and 25 µl of NEM. After 12 h at room temperature the solvent was removed and the residue distributed between water and ethyl acetate. The organic layer was dried with sodium sulfate, filtered and the solvent was removed. 1 ml of TFA was added to the residue and the mixture stirred for 2 h at room temperature. The product was precipitated by the addition of water and ethyl acetate, and filtered off to give 43 mg (49%) of the title compound.

MS: 653.3 (M+H)$^+$

The following example compounds were prepared analogously to the above examples.

Example compounds of the formula Ih:

Ih

| A | MS (M + H)$^+$ |
|---|---|
| Example 40 | (pyridin-4-ylmethyl)amino | 653.3 |
| Example 41 | benzylamino | 652.2 |
| Example 42 | 3-methoxybenzylamino | 682.2 |
| Example 43 | 4-chlorobenzylamino | 686.2 |
| Example 44 | 4-methoxybenzylamino | 682.3 |
| Example 45 | dimethylamino | 590.2 |
| Example 46 | hydroxy | 563.2 |
| Example 47 | n-propyloxy | 605.2 |

Example compounds of the formula Ii

Ii

| A | MS (M + H)$^+$ |
|---|---|
| Example 48 | dimethylamino | 524.3 |
| Example 49 | hydroxy | 497.3 |
| Example 50 | n-propyloxy | 539.3 |

Pharmacological Testing

The ability of the compounds of the formula I to inhibit factor Xa and/or factor VIIa or other enzymes like thrombin, plasmin, or trypsin can be assessed by determining the concentration of the compound of the formula I that inhibits enzyme activity by 50%, i.e., the IC$_{50}$ value, which is related to the inhibition constant K$_i$. Purified enzymes are used in chromogenic assays. The concentration of inhibitor that causes a 50% decrease in the rate of substrate hydrolysis is determined by linear regression after plotting the relative rates of hydrolysis (compared to the uninhibited control) versus the log of the concentration of the compound of formula I. For calculating the inhibition constant K$_i$, the IC$_{50}$ value is corrected for competition with substrate using the formula $K_i = IC_{50}/\{1+(\text{substrate concentration}/K_m)\}$ wherein K$_m$ is the Michaelis-Menten constant (Chen and Prusoff, *Biochem. Pharmacol.* 22 (1973), 3099–3108; I. H. Segal, *Enzyme Kinetics*, 1975, John Wiley & Sons, New York, 100–125; which are incorporated herein by reference).

a) Factor Xa Assay

In the assay for determining the inhibition of factor Xa activity TBS-PEG buffer (50 mM TRIS-Cl, pH 7.8, 200 mM NaCl, 0.05% (w/v) PEG-8000, 0.02% (w/v) NaN$_3$) was used. The IC$_{50}$ was determined by combining in appropriate wells of a Costar half-area microtiter plate 25 µl human factor Xa (Enzyme Research Laboratories, Inc.; South Bend, Ind.) in TBS-PEG; 40 μl 10% (v/v) DMSO in TBS-PEG (uninhibited control) or various concentrations of the compound to be tested diluted in 10% (v/v) DMSO in TBS-PEG; and substrate S-2765 (N(α)-benzyloxycarbonyl-D-Arg-Gly-L-Arg-p-nitroanilide; Kabi Pharmacia, Inc.; Franklin, Ohio) in TBS-PEG.

The assay was performed by pre-incubating the compound of interest of formula I plus enzyme for 10 min. The assay was then initiated by adding substrate to obtain a final volume of 100 μl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 μM.

b) Factor VIIa Assay

The inhibitory activity towards factor VIIa/tissue factor activity was determined using a chromogenic assay essentially as described in J. A. Ostrem et al., *Biochemistry* 37 (1998) 1053–1059, which is incorporated herein by reference. Kinetic assays were conducted at 25° C. in half-area microtiter plates (Costar Corp., Cambridge, Mass.) using a kinetic plate reader (Molecular Devices Spectramax 250). A typical assay consisted of 25 μl human factor VIIa and TF (5 nM and 10 nM, respective final concentrations) combined with 40 μl of inhibitor dilutions in 10% DMSO/TBS-PEG buffer (50 mM Tris, 15 mM NaCl, 5 mM $CaCl_2$, 0.05% PEG 8000, pH 8.15). Following a 15 minute preincubation period, the assay was initiated by the addition of 35 μl of the chromogenic substrate S-2288 (D-Ile-Pro-Arg-p-nitroanilide, Pharmacia Hepar Inc., 500 μM final concentration).

The following test results (inhibition constants $K_i$ (FXa) for inhibition of factor Xa and $K_i$ (FVIIa) for inhibition of factor VIIa) were obtained.

| Example Compound | $K_i$ (FXa) (μM) | $K_i$ (FVIIa) (μM) |
|---|---|---|
| Example 1 | 0.048 | 188 |
| Example 2 | 0.076 | |
| Example 3 | 0.67 | |
| Example 4 | 0.354 | 42 |
| Example 5 | 0.018 | 58 |
| Example 6 | 0.038 | 7.5 |
| Example 8 | 1.1 | |
| Example 11 | 0.192 | |
| Example 16 | 6.15 | |
| Example 32 | 13 | 13 |
| Example 34 | 0.75 | 9.8 |
| Example 39 | 0.445 | >200 |
| Example 45 | 0.031 | >200 |
| Example 46 | 0.059 | >200 |
| Example 47 | 0.021 | >200 |
| Example 48 | 0.56 | >200 |
| Example 50 | 0.729 | >200 |

The following tests can serve to investigate the inhibition of selected other coagulation enzymes and other serine proteases by the compounds of formula I and thus to determine their specificity.

c) Thrombin Assay

TBS-PEG buffer is used for this assay. The $IC_{50}$ is determined as above for the factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend, Ind.). The enzyme concentration is 175 μM.

d) Plasmin Assay

TBS-PEG buffer is used for this assay. The $IC_{50}$ is determined as described above for the factor Xa assay, except that the substrate is S-2251 (D-Val-L-Leu-L-Lys-p-nitroanilide; Kabi) and the enzyme is human plasmin (Kabi). The enzyme concentration is 5 nM and the substrate concentration is 300 μM.

e) Trypsin Assay

TBS-PEG buffer containing 10 mM $CaCl_2$ is used for this assay. The $IC_{50}$ is determined as described above in the factor Xa assay, except that the substrate is BAPNA (benzoyl-L-Arg-p-nitroanilide; Sigma Chemical Co.; St. Louis, Mo.) and the enzyme is bovine pancreatic trypsin (Type XIII, TPCK treated; Sigma). The enzyme concentration is 50 nM and the substrate concentration is 300 μM.

Rat Arteriovenous Shunt Model of Thrombosis

The antithrombotic efficacy of the compounds of the invention is assessed using rat extracorporeal arteriovenous (AV) shunt. The AV shunt circuit consists of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completing the circuit into the left jugular vein. The entire circuit is filled with normal saline prior to insertion.

The test compound is administered by continuous infusion into the tail vein using a syringe pump and butterfly catheter. The compound is administered for 30 min, then the shunt is opened and blood allowed to flow for a period of 15 min (total of 45 min infusion). At the end of the 15 min period, the shunt is clamped and the thread is carefully removed and weighed on an analytical balance. Percent inhibition of thrombus formation is calculated using the thrombus weight obtained from control rats, which are infused with saline.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A compound of the formula I

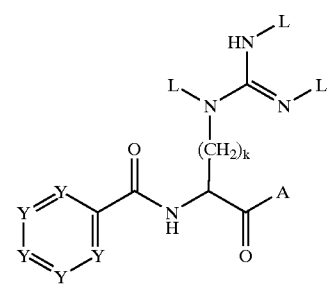

wherein:
one or two of the Y groups are carbon atoms bonded to a group of the formula II, $$R^0—(CH_2)_n—O—\qquad\qquad II$$

zero of the Y groups are nitrogen atoms, and the remaining Y groups are carbon atoms bonded to a group $R^1$, where the Y groups are selected independently of one another and are identical or different;

L is selected from hydrogen, $(C_1-C_8)$-alkylcarbonyl, $(C_6-C_{14})$-aryl-$(C_1-C_4)$-alkylcarbonyl, $(C_6-C_{14})$-arylcarbonyl, $(C_1-C_8)$-alkyloxycarbonyl, $(C_6-C_{14})$-aryl-$(C_1-C_4)$-alkyloxycarbonyl, and $(C_6-C_{14})$-aryloxycarbonyl, where aryl groups present in L are unsubstituted, or substituted by one or more identical or different substituents $R^{13}$, and where all L groups are selected independently of each other and are identical or different;

A is selected from $R^3O—$ and $R^4R^5N—$;

k is 1, 2, 3, or 4;

n is 0, 1, 2, 3, or 4;

$R^0$ is selected from phenyl, and monocyclic 6-membered heteroaryl containing one or two nitrogen atoms as ring heteroatoms, where the group $R^0$ is unsubstituted, or substituted by one or more identical or different groups $R^2$;

$R^1$ is selected from hydrogen, halogen, nitro, hydroxy, $(C_1-C_8)$-alkyloxy-, $(C_6-C_{14})$-aryl, $(C_1-C_8)$-alkyl, hydroxycarbonyl-$(C_1-C_8)$-alkylureido-, $(C_1-C_8)$-alkyloxycarbonyl-$(C_1-C_8)$-alkylureido-, $(C_1-C_8)$-alkylsulfonyl-, and $R^{11}R^{12}N—$, where the $R^1$ groups are selected independently of each other and can be identical or different, and where alkyl and aryl groups present in $R^1$ are unsubstituted, or substituted by one or more identical or different substituents $R^{13}$, or two $R^1$ groups bonded to adjacent ring carbon atoms, together with the carbon atoms to which they are bonded, form an aromatic ring fused to the ring of formula I, where the ring formed by the two $R^1$ groups is unsubstituted, or substituted by one or more identical or different substituents $R^{13}$;

$R^2$ is selected from halogen, nitro, $(C_1-C_8)$-alkyl, cyano, hydroxy, amino, and $(C_1-C_8)$-alkyloxy-, where alkyl groups present in $R^2$ are unsubstituted, or substituted by one or more identical or different halogen atoms;

$R^3$, $R^4$, and $R^5$ are selected from hydrogen, $(C_1-C_{12})$-alkyl, $(C_6-C_{14})$-aryl-$(C_1-C_4)$-alkyl, $(C_6-C_{14})$-aryl-, Het-, and Het-$(C_1-C_4)$-alkyl-, where $R^4$ and $R^5$ are selected independently of each other, and can be identical or different, and wherein any groups alkyl, aryl, and Het present in $R^3$, $R^4$, and $R^5$ are unsubstituted, or substituted by one or more identical or different substituents $R^{13}$, or $R^4$ and $R^5$, together with the nitrogen atom to which they are bonded, form a saturated 3-membered to 8-membered monocyclic heterocyclic ring, which, in addition to the nitrogen atom bonded to $R^4$ and $R^5$, optionally contains one or two identical or different ring heteroatom(s) selected from oxygen, sulfur, and nitrogen;

$R^{11}$ and $R^{12}$, which are selected independently of each other, and which are identical or different, are selected from hydrogen, $(C_1-C_8)$-alkyl, $(C_6-C_{14})$-aryl-$(C_1-C_4)$-alkyl-, Het-$(C_1-C_4)$alkyl-, hydroxycarbonyl-$(C_1-C_8)$-alkyl-, $(C_1-C_8)$-alkyloxycarbonyl-$(C_1-C_8)$-alkyl, hydroxycarbonyl-$(C_1-C_8)$-alkylcarbonyl-, $(C_1-C_8)$-alkyloxycarbonyl-$(C_1-C_8)$-alkylcarbonyl-, and $(C_1-C_8)$-alkylcarbonyl-, wherein any alkyl and aryl groups present in $R^{11}$ and $R^{12}$ are unsubstituted, or substituted by one or more identical or different substituents $R^{13}$, or $R^{11}$ and $R^{12}$, together with the nitrogen atom to which they are bonded, form a saturated or unsaturated 5-membered to 8-membered monocyclic heterocyclic ring, which, in addition to the nitrogen atom carrying $R^{11}$ and $R^{12}$, optionally contains one or two identical or different ring heteroatoms selected from oxygen, sulfur, and nitrogen, and wherein one or two ring carbon atoms are optionally substituted by oxo to form C=O group (s);

$R^{13}$ is selected from halogen, nitro, cyano, hydroxy, $(C_1-C_8)$-alkyl, $(C_1-C_8)$-alkyloxy, trifluoromethyl, and amino; and Het is a residue of a saturated, partially unsaturated, or aromatic monocyclic or bicyclic, 3-membered to 10-membered heterocyclic ring system containing one, two, three, or four identical or different heteroatoms selected from nitrogen, oxygen, and sulfur;

or any stereoisomeric form, a physiologically tolerable salt, or a mixture thereof in any ratio.

2. A compound as claimed in claim 1, wherein one of the Y groups is a carbon atom bonded to a group of the formula II, or any stereoisomeric form, a physiologically tolerable salt, or a mixture thereof in any ratio.

3. A compound as claimed in claim 1, wherein $R^1$ is selected from hydrogen, halogen, hydroxy, nitro, $R^{11}R^{12}N—$, and $(C_1-C_8)$-alkyloxy, or any stereoisomeric form, a physiologically tolerable salt, or a mixture thereof in any ratio.

4. A compound as claimed in claim 1, wherein A is $R^4R^5N—$, or any stereoisomeric form, a physiologically tolerable salt, or a mixture thereof in any ratio.

5. A compound as claimed in claim 1, wherein one of the Y groups is a carbon atom bonded to a group of the formula II,

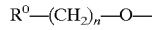

zero of the Y groups are nitrogen atoms, and the remaining Y groups are carbon atoms bonded to a group $R^1$, where the Y groups are selected independently of each other and are identical or different;

A is $R^4R^5N—$;

k is 3;

n is 2; and $R^0$ is phenyl, which is unsubstituted, or substituted by one or two identical or different substituents;

or any stereoisomeric form, a physiologically tolerable salt, or a mixture thereof in any ratio.

6. A process for the preparation of a compound as claimed in claim 1, comprising linking compounds of the formulae IV, V, VI, and VII:

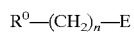

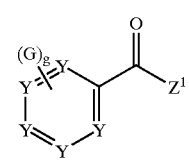

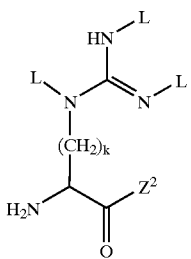

VI

H—A  VII wherein $R^0$, A, L, k, and n are defined as in claim 1, one or two of the Y groups in the compounds of the formula V are carbon atom(s) to which G groups are bonded, zero of the Y groups are nitrogen atoms, and the remaining Y groups are carbon atoms carrying an $R^1$ group, where $R^1$ is defined as in claim 1, but where functional groups in $R^0$, $R^1$, A, and L are optionally present in protected form or in the form of precursor groups, and in which one of the two groups E and G is hydroxy, and the other is hydroxy, or a nucleophilically substitutable leaving group, g is one or two, and $Z^1$ and $Z^2$ are hydroxy or nucleophilically substitutable leaving groups.

7. A pharmaceutical composition, comprising an effective amount of at least one compound as claimed in claim 1, or any stereoisomeric form, a physiologically tolerable salt, or a mixture thereof in any ratio, and a pharmaceutically acceptable carrier.

* * * * *

UNITED STATES PATENT AND TRADEMARK OFFICE
CERTIFICATE OF CORRECTION

PATENT NO.    : 6,472,562 B1
DATED         : October 29, 2002
INVENTOR(S)   : Klingler et al.

It is certified that error appears in the above-identified patent and that said Letters Patent is hereby corrected as shown below:

<u>Title page,</u>
Item [57], ABSTRACT,
Line 17, after "in particular" and before "active ingredients", insert -- as --.

<u>Column 43,</u>
Line 12, "1 ," should read -- 1, --.
Line 39, "$(C_6-C_{14})$-aryl-$(C_1-C_4)$-alkyl," should read -- $(C_6-C_{14})$-aryl-$(C_1-C_4)$-alkyl-, --.
Line 58, "$(C_1-C_8)$-alkyloxycarbonyl-$(C_1-C_8)$-alkyl," should read -- $(C_1-C_8)$-alkyloxycarbonyl-$(C_1-C_8)$-alkyl-, --.

<u>Column 44,</u>
Lines 5-6, "group (s);" should read -- group(s); --.

Signed and Sealed this

Twentieth Day of May, 2003

JAMES E. ROGAN
*Director of the United States Patent and Trademark Office*